US012630553B2

(12) United States Patent
Wen et al.

(10) Patent No.: US 12,630,553 B2
(45) Date of Patent: May 19, 2026

(54) CRYSTALLINE FORMS OR AMORPHOUS FORMS OF BISDIAZABICYCLIC COMPOUNDS OR SALTS THEREOF

(71) Applicants:Ascentage Pharma (Suzhou) Co., Ltd., Suzhou (CN); Ascentage Pharma Group Corp Limited, Hong Kong (CN)

(72) Inventors: Jianfeng Wen, Jiangsu (CN); Yanqiong Lin, Jiangsu (CN); Tianzhu Wu, Jiangsu (CN); Minmin Cai, Jiangsu (CN); Zongbin Li, Jiangsu (CN); Weidong Li, Jiangsu (CN)

(73) Assignees: Ascentage Pharma (Suzhou) Co., Ltd., Suzhou (CN); Ascentage Pharma Group Corp Limited, Hong Kong (CN)

( * ) Notice: Subject to any disclaimer, the term of this patent is extended or adjusted under 35 U.S.C. 154(b) by 672 days.

(21) Appl. No.: 18/016,013

(22) PCT Filed: Jul. 16, 2021

(86) PCT No.: PCT/CN2021/106773
§ 371 (c)(1),
(2) Date: Jan. 13, 2023

(87) PCT Pub. No.: WO2022/012671
PCT Pub. Date: Jan. 20, 2022

(65) Prior Publication Data
US 2023/0257384 A1      Aug. 17, 2023

(30) Foreign Application Priority Data
Jul. 16, 2020    (CN) .......................... 202010687449.5
Jul. 9, 2021    (CN) .......................... 202110774958.6

(51) Int. Cl.
*C07D 487/04* (2006.01)

(52) U.S. Cl.
CPC ........ *C07D 487/04* (2013.01); *C07B 2200/13* (2013.01)

(58) Field of Classification Search
CPC ..................................................... C07D 487/04
USPC .......................................................... 514/413
See application file for complete search history.

(56) References Cited

FOREIGN PATENT DOCUMENTS

| | | | | |
|---|---|---|---|---|
| WO | 2014/031487 | A1 | 2/2014 | |
| WO | 2019/101047 | A1 | 5/2019 | |
| WO | 2020/109328 | A1 | 6/2020 | |
| WO | WO-2021204060 | A1 * | 10/2021 | ............. A61K 38/06 |

OTHER PUBLICATIONS

Liu et al., Targeting cIAPs, a New Option for Functional Cure of Chronic Hepatitis B Infection?, Virologica Sinica, 2018, vol. 33, pp. 459-461 (Year: 2018).*
Pan et al., A novel SMAC mimetic APG-1387 exhibits dual anti-tumor effect on HBV-positive hepatocellular carcinoma with high expression of cIAP2 by inducing apoptosis and enhancing innate anti-tumor immunity, Biochemical Pharmacology, 2018, vol. 154, pp. 127-135 (Year: 2018).*
Li et al., A novel Smac mimetic APG-1387 demonstrates potent antitumor activity in nasopharyngeal carcinoma cells by inducing apoptosis. Cancer Lett. Oct. 10, 2016;381(1):14-22.
International Search Report and Written Opinion for Application No. PCT/CN2021/106773, dated Oct. 27, 2021, 7 pages.

* cited by examiner

*Primary Examiner* — Jeffrey H Murray
*Assistant Examiner* — Rilla Marie Samsell
(74) *Attorney, Agent, or Firm* — McCarter & English, LLP; Wei Song

(57) ABSTRACT

Crystallines form or amorphous forms of bisdiazabicyclic compounds or salts thereof for the treatment and/or prevention of diseases or disorders related to hepatitis virus, and a preparation method and application thereof are provided. The crystalline forms or amorphous forms involved provide important reference value for the development and utilization of drugs in the future.

20 Claims, 30 Drawing Sheets

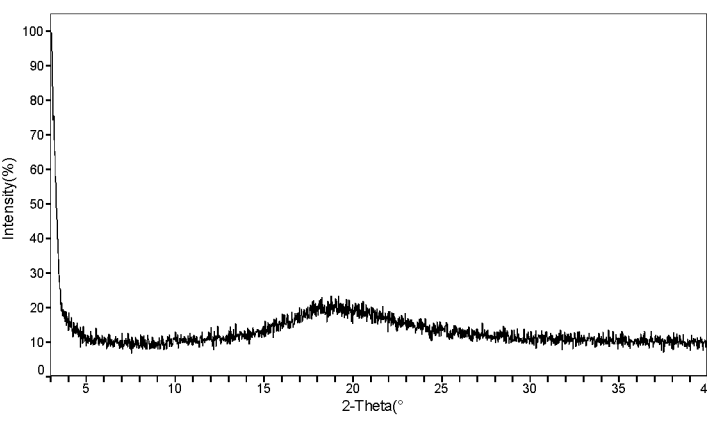
FIG.64
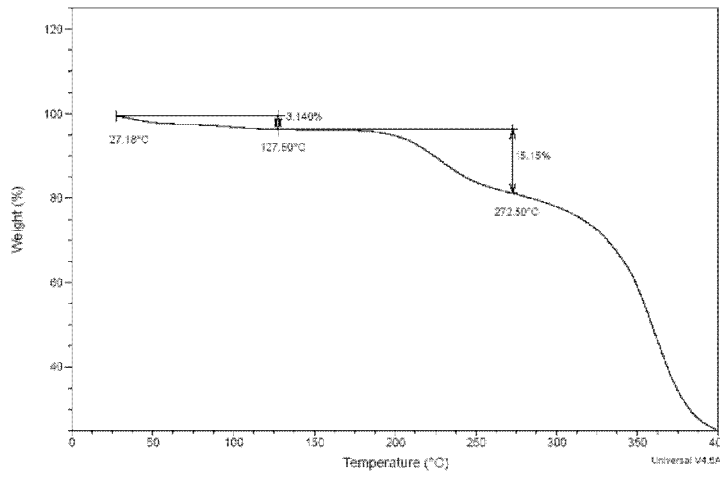
FIG.65
FIG.66

1

CRYSTALLINE FORMS OR AMORPHOUS FORMS OF BISDIAZABICYCLIC COMPOUNDS OR SALTS THEREOF

CROSS REFERENCE TO RELATED APPLICATIONS

This application is a U.S. National Stage Application filed under 35 U.S.C. § 371, based on International Patent Application No. PCT/CN2021/106773, filed on Jul. 16, 2021, which claims priority to CN patent application Ser. No. 20/201,0687449.5, filed on Jul. 16, 2020, and CN patent application Ser. No. 20/211,0774958.6, filed on Jul. 9, 2021.

FIELD OF THE INVENTION

The present invention belongs to the field of medicinal chemistry, and particularly relates to the crystalline forms or amorphous forms of bisdiazabicyclic compounds or its salt for the treatment and/or prevention of diseases or disorders related to hepatitis virus, as well as the preparation method and application thereof.

BACKGROUND OF THE INVENTION

Hepatitis or liver disease is a disease usually caused by hepatitis virus. Hepatitis virus can usually be divided into types A, B, C, D, E, and G. Among them, Chronic disease caused by the hepatitis B virus is currently distributed throughout the world. If improperly controlled, a considerable proportion of hepatitis B will be transformed into liver cancer in the later stage of the disease.

According to the 2015 China Chronic Hepatitis B (CHB) Prevention and Treatment Guidelines, the goal of chronic hepatitis B treatment is to minimize HBV replication for a long time, reduce hepatocyte inflammatory necrosis and liver fibrosis, and delay and reduce liver failure, decompensation of liver cirrhosis, HCC and other complications, thereby improving the quality of life and prolonging survival time. In the course of treatment, for some suitable patients, the clinical cure of chronic hepatitis B should be pursued as much as possible, that is, continuous virological response after stopping treatment, HBsAg negative conversion or accompanied by anti-HBs positive conversion, normal ALT, mild liver tissue disease or No lesions. The complete cure refers to the elimination of HBV DNA, various antigens, and cccDNA in addition to antibodies.

At present, the US FDA has approved 7 antiviral drugs for the treatment of chronic hepatitis B infection, including common and long-acting interferons and 5 oral nucleoside (acid) analogues: lamivudine, adefovir dipivoxil, entecavir, Telbivudine and tenofovir disoproxil fumarate, among which entecavir and tenofovir disoproxil fumarate are recommended as first-line drugs as the first-line treatment. However, in clinical use of existing nucleoside (acid) analog drugs for 5 years, the HBsAg negative returning rate is less than 5%; for those who respond after receiving long-acting interferon (PEG-IFN) treatment, the HBsAg negative returning rate during long-term follow-up is also less than 10%. For CHB patients, nucleoside (acid) analog drugs can only inhibit the synthesis of the positive and negative strands of the virus in the nucleocapsid. In the process of antiviral therapy, the main thing that disappears is the replicating DNA, it has no direct effect on the cccDNA in the nucleus of liver cells and the viral antigens expressed by transcription. Another type of drug, IFNα, has both immune regulation and direct antiviral effects. It can induce the expression of APOBEC3A in HBV-infected hepatocytes, and promote the degradation of cccDNA through base editing to exert a direct antiviral effect. However, HBV has been proven to antagonize the IFNα signaling pathway, leading to poor therapeutic effects of IFNα drugs. Therefore, taking into account the limitations of current antiviral drugs, other treatment strategies to eliminate chronic HBV infection are the hotspot of research currently. Correspondingly, there is also an urgent need for new drugs for treating hepatitis virus in this field.

CN109467566A discloses bisdiazabicyclic compounds for the treatment and/or prevention of diseases or disorders related to hepatitis virus, and specifically discloses representative compounds: 1,3-benzenedi[7-(3 S,5 S,9aR)-5-((S)-2-methylamino-propionamido)-3-dibenzamido-4-oxo-3a,7-diaza-decahydrocyclopentacyclooctene)]-sulfonamide, its structural formula is as follows:

However, the current literature including the patent application, mainly reported the structure and pharmacological activity of the compounds without any studies and reports on polymorphs, amorphous and other structural forms.

Due to the influence of various factors such as configuration, conformation, molecular arrangement, molecular interaction and eutectic mixtures of molecular structure of solid matter, the arrangement of molecular lattice space is different and two or more different crystal structures are formed. This Phenomenon is called "Polymorphism Phenomenon" or "allomorphism"." Polymorphism phenomenon" widely exists in solid drugs. Physical and chemical properties between different crystal forms of the same drug can exist differences, such as appearance, density, hardness, melting point, solubility, stability, dissolution, dissolution rate and bioavailability can be significantly different. This phenomenon is particularly evident in oral solid preparations. Further more, the existent forms and quantities of polycrystalline compounds are unpredictable. Different crystalline forms of the same drug have significant differences in solubility, melting point, density, stability, etc., which affect the uniformity, bioavailability, efficacy and safety etc. of the drug to different degrees.

In addition to polycrystalline form, some solid compounds may have amorphous forms. The amorphous refers to the structure of some amorphous regions (amorphous regions) of incomplete crystals or forms of some amorphous In addition, when referring to, for example, XRPD patterns, TGA plots, DSC curves, mDSC curves, ion Chromatography, Liquid NMR etc., the terms "substantially as shown" mean that they are not necessarily the same as those described herein, but when considered by ordinary persons skilled in the art, the spectrum falls within the limits of experimental error or deviation.

In the first aspect, the present invention provides the amorphous or crystalline forms of the compound 1 below or its salts:

(compound 1)

solids (amorphous regions). For a specific solid drug, the existent forms and quantities of its amorphous form are also unpredictable, and may also have a significant impact on the solubility, melting point, density, stability, etc.

Therefore, in the process of new drug research and development, it is necessary to consider multiple factors to carry out comprehensive screening of the crystalline forms and amorphous forms of drug compounds. In particular, for the above compound 1 used in the treatment and/or prevention of diseases or disorders related to hepatitis virus, there are potential medicinal values and clinical values to develop crystalline or amorphous forms of the compound or their salts with possible medical values to improve the stability, solubility, bioavailability and other properties of the compounds.

SUMMARY OF THE INVENTION

The present invention provides crystalline forms or amorphous forms of bisdiazabicyclic compounds or its salts for the treatment and/or prevention of diseases or disorders related to hepatitis virus, as well as preparation methods and applications thereof. The crystalline forms or amorphous forms of the invention are of great values for drug development, formulation development and production.

In the following descriptions, certain specific details are described to provide thorough understandings of the various embodiments of the invention. However, the persons skilled in the art will understand that the invention can be practiced without the details. The following descriptions of several embodiments are done with the understanding that the present disclosure is regarded as an example of the subject matter for which protection is sought, and is not intended to limit the attached claims to the particular embodiments shown. The headings used throughout the invention are provided for convenience only and shall not be construed as limiting claims in any way. The embodiments shown under any heading may be combined with the embodiments shown under any other heading.

As used herein, "Compound 1" refers to a compound having a chemical name 1,3-benzenedi[7-(3S,5S,9aR)-5-((S)-2-methylamino-propionamido)-3-dibenzamido-4-oxo-3a,7-diaza-decahydrocyclopentacyclooctene)]-sulfonamide.

Specifically, the forms can be the following specific forms:

1) The Crystalline Form I of Compound 1

In one embodiment, the form is the crystalline form I of the compound 1(free base), which is characterized by having at least three, at least four, at least five, at least six characteristic peaks at the following positions in the X-ray powder diffraction (XRPD) pattern represented by angle 2θ: 7.93±0.2°, 9.60±0.2°, 11.27±0.2°, 15.73±0.2°, 18.63±0.2° and 19.22±0.2°.

In some preferred embodiments, the form also has one or more characteristic peaks at the following positions in the XRPD pattern represented by angle 2θ: 11.92±0.2°, 12.52±0.22 and 16.72±0.2°.

In some preferred embodiments, the form has XRPD characteristic peaks at the positions substantially as shown in Table 1 below and/or an X-ray powder diffraction (XRPD) pattern substantially as shown in FIG. 1.

TABLE 1

| Angle[°2θ] ±0.2° | d-value[Å] | Relative intensity [%] |
| --- | --- | --- |
| 7.93 | 11.15 | 100.00 |
| 9.60 | 9.21 | 36.45 |
| 11.27 | 7.85 | 26.93 |
| 11.92 | 7.42 | 19.95 |
| 12.52 | 7.07 | 12.33 |
| 15.73 | 5.64 | 23.89 |
| 16.72 | 5.30 | 11.30 |
| 18.63 | 4.76 | 25.43 |
| 19.22 | 4.62 | 51.03 |
| 23.21 | 3.83 | 9.74 |
| 26.94 | 3.31 | 6.29 |

In some preferred embodiments, it also has the following characteristics:

1) In the thermogravimetric analysis (TGA) plot, there is a weight loss of 1.6±0.2% by weight before 130° C.;

2) In the DSC curve, there are 2 endothermic peaks at the peak temperature of 67.0±2.0° C. and 174.1±2.0° C.;

3) the TGA plot substantially as shown in FIG. 2; and/or 4) the DSC curve substantially as shown in FIG. 3.

2) The Crystalline Form II of Compound 1

In one embodiment, the form is the crystalline form II of the compound 1(free base), which is characterized by having at least one, or at least two characteristic peaks at the following positions in the XRPD pattern represented by angle 2θ: 5.80±0.2° and 7.68±0.2°.

In some preferred embodiments, the form has XRPD characteristic peaks at the positions substantially as shown in Table 2 below and/or an XRPD pattern substantially as shown in FIG. 4.

TABLE 2

| Angle [°2θ] ±0.2° | d-value [Å] | Relative intensity [%] |
|---|---|---|
| 5.80 | 15.23 | 100.00 |
| 7.68 | 11.52 | 67.83 |

In some preferred embodiments, it also has the following characteristics:

1) In the TGA plot, there is a weight loss of 5.4±0.2% by weight before 130° C.;

2) In the DSC curve, there are two endothermic peaks at the peak temperatures of 69.5±2.0° C. and 150.7±2.0° C.;

3) the TGA plot substantially as shown in FIG. 5; and/or 4) the DSC curve substantially as shown in FIG. 6.

3) The Crystalline Form III of Compound 1

In one embodiment, the form is the crystalline form III of the compound 1(free base), which is characterized by having at least three, at least four or five characteristic peaks at the following positions in the XRPD pattern represented by angle 2θ: 7.83±0.22, 9.78±0.22, 11.78±0.22, 19.32±0.22 and 19.68±0.22.

In some preferred embodiments, the form has XRPD characteristic peaks at the positions substantially as shown in Table 3 below and/or an XRPD pattern substantially as shown in FIG. 7.

TABLE 3

| Angle [°2θ] ±0.2° | d-value [Å] | Relative intensity [%] |
|---|---|---|
| 7.83 | 11.29 | 100.00 |
| 9.78 | 9.05 | 31.95 |
| 11.40 | 7.76 | 11.90 |
| 11.78 | 7.51 | 20.01 |
| 12.76 | 6.94 | 6.29 |
| 16.63 | 5.33 | 7.78 |
| 17.51 | 5.06 | 5.75 |
| 19.32 | 4.59 | 28.93 |
| 19.68 | 4.51 | 19.35 |
| 21.00 | 4.23 | 4.12 |
| 24.50 | 3.63 | 2.52 |
| 26.16 | 3.41 | 3.80 |

In some preferred embodiments, it also has the following characteristics:

1) In the TGA plot, there is a weight loss of 17.2±0.2% by weight before 140° C.;

2) In the DSC curve, there are two endothermic peaks at the peak temperatures of 90.7±2.0° C. and 172.6±2.0° C.;

3) the TGA plot substantially as shown in FIG. 8; and/or 4) the DSC curve substantially as shown in FIG. 9.

4) The Amorphous Form IV of Compound 1 Monohydrochloride

In one embodiment, the form is the amorphous form IV of the compound 1 monohydrochloride, characterized in that it has an XRPD pattern substantially as shown in FIG. 10.

In some preferred embodiments, it also has the following characteristics:

1) In the TGA plot, there is a weight loss of 7.9±0.2% by weight before 150° C.;

2) In the mDSC curve, there is a glassy transition temperature at the midpoint temperature of 184.6±2.0° C.;

3) the TGA plot substantially as shown in FIG. 11; and/or 4) the mDSC curve substantially as shown in FIG. 12.

In one embodiment, ion chromatography (IC) results show that the molar ratio of hydrochloric acid to the compound 1 in Form IV is 1.3:1.

5) The Amorphous Form V of Compound 1 Dihydrochloride

In one embodiment, the form is the amorphous form V of the compound 1 dihydrochloride, characterized in that it has an XRPD pattern substantially as shown in FIG. 13.

In some preferred embodiments, it also has the following characteristics:

1) In the TGA plot, there is a weight loss of 6.6±0.2% by weight before 150° C.;

2) In the mDSC curve, there is a glassy transition temperature at the midpoint temperature of 213.0±2.0° C.;

3) the TGA plot substantially as shown in FIG. 14; and/or 4) the mDSC curve substantially as shown in FIG. 15.

In one embodiment, ion chromatography (IC) results show that the molar ratio of hydrochloric acid to the compound 1 in Form V is 2.1:1.

6) The Amorphous Form VI of Compound 1 Sulfate

In one embodiment, the form is the amorphous form VI of the compound 1 sulfate, characterized in that it has an XRPD pattern substantially as shown in FIG. 16.

In some preferred embodiments, it also has the following characteristics:

1) In the TGA plot, there is a weight loss of 9.6±0.2% by weight before 150° C.;

2) In the mDSC curve, there is a glassy transition temperature at the midpoint temperature of 207.2±2.0° C.;

3) the TGA plot substantially as shown in FIG. 17; and/or 4) the mDSC curve substantially as shown in FIG. 18.

In one embodiment, ion chromatography (IC) results show that the molar ratio of sulfuric acid to the compound 1 in Form VI is 1.3:1.

7) The Amorphous Form VII of Compound 1 Phosphate

In one embodiment, the form is the amorphous form VII of the compound 1 phosphate, characterized in that it has an XRPD pattern substantially as shown in FIG. 19.

In some preferred embodiments, it also has the following characteristics:

1) In the TGA plot, there is a weight loss of 4.5±0.2% by weight before 150° C.;

2) In the mDSC curve, there is a glassy transition temperature at the midpoint temperature of 176.0±2.0° C.;

3) the TGA plot substantially as shown in FIG. 20; and/or 4) the mDSC curve substantially as shown in FIG. 21.

In one embodiment, ion chromatography (IC) results show that the molar ratio of phosphoric acid to the compound 1 in Form VII is 1.6:1.

8) The Amorphous Form VIII of Compound 1 Mesylate

In one embodiment, the form is the amorphous form VIII of the compound 1 mesylate, characterized in that it has an XRPD pattern substantially as shown in FIG. 22.

In some preferred embodiments, it also has the following characteristics:

1) In the TGA plot, there is a weight loss of 5.2±0.2% by weight before 150° C.;

2) In the mDSC curve, there is a glassy transition temperature at the midpoint temperature of 172.7±2.0° C.;

3) the TGA plot substantially as shown in FIG. 23; and/or 4) the mDSC curve substantially as shown in FIG. 24.

In one embodiment, liquid NMR (use Bruker 400M nuclear magnetic resonance instrument to collect, use DMSO-d6 as solvent) results show that the molar ratio of methanesulfonic acid to the compound 1 in Form VIIII is 2.1:1, and no solvent residues are detected.

9) The Amorphous Form IX of Compound 1 Maleate

In one embodiment, the form is the amorphous form IX of the compound 1 maleate, characterized in that it has an XRPD pattern substantially as shown in FIG. 25.

In some preferred embodiments, it also has the following characteristics:

1) In the TGA plot, there is a weight loss of 3.7±0.2% by weight before 150° C.;

2) In the mDSC curve, there is a glassy transition temperature at the midpoint temperature of 163.6±2.0° C.;

3) the TGA plot substantially as shown in FIG. 26; and/or 4) the mDSC curve substantially as shown in FIG. 27.

In one embodiment, liquid NMR results show that the molar ratio of maleic acid to the compound 1 in Form IX is 0.8:1, and no solvent residues are detected.

10) The Amorphous Form X of Compound 1 Tartrate

In one embodiment, the form is the amorphous form X of the compound 1 tartrate, characterized in that it has an XRPD pattern substantially as shown in FIG. 28.

In some preferred embodiments, it also has the following characteristics:

1) In the TGA plot, there is a weight loss of 8.3±0.2% by weight before 150° C.;

2) In the mDSC curve, there is a glassy transition temperature at the midpoint temperature of 163.9±2.0° C.;

3) the TGA plot substantially as shown in FIG. 29; and/or 4) the mDSC curve substantially as shown in FIG. 30.

In one embodiment, liquid NMR results show that the molar ratio of tartaric acid to the compound 1 in Form X is 1.9:1, and no solvent residues are detected.

11) the Amorphous Form XI of Compound 1 Benzoate

In one embodiment, the form is the amorphous form XI of the compound 1 benzoate, characterized in that it has an XRPD pattern substantially as shown in FIG. 31.

In some preferred embodiments, it also has the following characteristics:

1) In the TGA plot, there is a weight loss of 9.1±0.2% by weight before 150° C.;

2) In the mDSC curve, there is a glassy transition temperature at the midpoint temperature of 143.8±2.0° C.;

3) the TGA plot substantially as shown in FIG. 32; and/or 4) the mDSC curve substantially as shown in FIG. 33.

In one embodiment, liquid NMR results show that the molar ratio of benzoic acid to the compound 1 in Form XI is 0.8:1, and the molar ratio of MTBE to the compound 1 is 0.04:1, corresponding to a weight loss of 0.3% by weight.

12) The Amorphous Form XII of Compound 1 Succinate

In one embodiment, the form is the amorphous form XII of the compound 1 succinate, characterized in that it has an XRPD pattern substantially as shown in FIG. 34.

In some preferred embodiments, it also has the following characteristics:

1) In the TGA plot, there is a weight loss of 3.5±0.2% by weight before 150° C.;

2) In the mDSC curve, there is a glassy transition temperature at the midpoint temperature of 138.9±2.0° C.;

3) the TGA plot substantially as shown in FIG. 35; and/or 4) the mDSC curve substantially as shown in FIG. 36.

In one embodiment, liquid NMR results show that the molar ratio of succinic acid to the compound 1 in Form XII is 1.2:1, and no solvent residues are detected.

13) The Amorphous Form XIII of Compound 1 Acetate

In one embodiment, the form is the amorphous form XIII of the compound 1 acetate, characterized in that it has an XRPD pattern substantially as shown in FIG. 37.

In some preferred embodiments, it also has the following characteristics:

1) In the TGA plot, there is a weight loss of 8.0±0.2% by weight before 150° C.;

2) In the mDSC curve, there is a glassy transition temperature at the midpoint temperature of 137.9±2.0° C.;

3) the TGA plot substantially as shown in FIG. 38; and/or 4) the mDSC curve substantially as shown in FIG. 39.

In one embodiment, liquid NMR results show that the molar ratio of acetic acid to the compound 1 in Form XIII is 1.0:1. and no solvent residues are detected.

14) The Amorphous Form XIV of Compound 1

In one embodiment, the form is the amorphous form XIV of the compound 1, characterized in that it has an XRPD pattern substantially as shown in FIG. 40.

In some preferred embodiments, it also has the following characteristics:

1) In the TGA plot, there is a weight loss of 4.2±0.2% by weight before 130° C.;

2) In the mDSC curve, there is a glassy transition temperature at the midpoint temperature of 145.2±2.0° C.;

3) the TGA plot substantially as shown in FIG. 41; and/or 4) the mDSC curve substantially as shown in FIG. 42.

15) The Amorphous Form XV of Compound 1 Mono-p-toluenesulfonate

In one embodiment, the form is the amorphous form XV of compound 1 mono-p-toluenesulfonate, characterized in that it has an XRPD pattern substantially as shown in FIG. 43.

In some preferred embodiments, it also has the following characteristics:

1) In the TGA plot, there is a weight loss of 2.55±0.2% by weight before 127° C.; and a weight loss of 2.51±0.2% by weight between 127° C. and 222° C.;

2) In the mDSC curve, there is a glassy transition temperature at the midpoint temperature of 150.82±2.0° C.;

3) the TGA plot substantially as shown in FIG. 44; and/or 4) the mDSC curve substantially as shown in FIG. 45.

In one embodiment, 1H-NMR results show that the molar ratio of the compound 1 and p-toluenesulfonic acid is 1:1.25.

16) The Amorphous Form XVI of Compound 1 Di-p-Toluenesulfonate

In one embodiment, the form is the amorphous form XVI of compound 1 di-p-toluenesulfonate, characterized in that it has an XRPD pattern substantially as shown in FIG. 46.

In some preferred embodiments, it also has the following characteristics:

1) In the TGA plot, there is a weight loss of 2.97±0.2% by weight before 125° C.;

2) In the mDSC curve, there is a glassy transition temperature at the midpoint temperature of 168.02±2.0° C.;

3) the TGA plot substantially as shown in FIG. 47; and/or 4) the mDSC curve substantially as shown in FIG. 48.

In one embodiment, 1H-NMR results showed that the molar ratio of the compound 1 to p-toluenesulfonic acid in Form XVI was 1:2.19.

17) The Amorphous Form XVII of Compound 1 Diphosphate

In one embodiment, the form is the amorphous form XVII of compound 1 diphosphate, characterized in that it has an XRPD pattern substantially as shown in FIG. 49.

In some preferred embodiments, it also has the following characteristics:

1) In the TGA plot, there is a weight loss of 1.46±0.2% by weight before 140° C.;

2) In the mDSC curve, there is a glassy transition temperature at the midpoint temperature of 177.83±2.0° C.;

3) the TGA plot substantially as shown in FIG. 50; and/or 4) the mDSC curve substantially as shown in FIG. 51.

18) the Crystalline Form XVIII of Compound 1 Dimethanesulfonate

In one embodiment, the form is the crystalline form XVIII of compound 1 dimethanesulfonate, which has at least one or two characteristic peaks at the following positions in the XRPD pattern represented by angles 2θ: 3.94±0.2°, 5.53±0.2°, 11.45±0.2°, 15.25±0.2°, 20.51±0.2°.

In some preferred embodiments, the form has XRPD characteristic peaks at the positions substantially as shown in Table 4 and/or the XRPD pattern substantially as shown in FIG. 52.

In some preferred embodiments, it also has the following characteristics:

1) In the TGA plot, there is a weight loss of 5.35±0.2% by weight before 142° C.;

2) In the mDSC curve, there is a broad melting peak at the initial temperature of 126.70±2.0° C.;

3) the TGA plot substantially as shown in FIG. 53; and/or 4) the mDSC curve substantially as shown in FIG. 54.

In one embodiment, 1H-NMR results showed that the molar ratio of the compound 1 to methanesulfonic acid is 1:1.94.

TABLE 4

| Angle [°2θ] ±0.2° | d-Value[Å] | Relative intensity [%] |
|---|---|---|
| 3.94 | 22.43 | 100.00 |
| 5.53 | 15.97 | 47.10 |
| 7.71 | 11.46 | 10.30 |
| 10.95 | 8.07 | 18.90 |
| 11.45 | 7.72 | 72.20 |
| 12.66 | 6.99 | 28.40 |
| 14.26 | 6.21 | 10.50 |
| 14.80 | 5.98 | 46.80 |
| 15.25 | 5.80 | 65.20 |
| 16.11 | 5.50 | 19.60 |
| 17.43 | 5.08 | 12.50 |
| 18.22 | 4.87 | 43.30 |
| 19.15 | 4.63 | 10.80 |
| 20.51 | 4.33 | 47.90 |
| 21.47 | 4.14 | 26.80 |
| 22.50 | 3.95 | 17.70 |
| 22.75 | 3.91 | 35.30 |
| 23.80 | 3.74 | 19.30 |
| 24.82 | 3.58 | 14.40 |
| 25.25 | 3.52 | 28.20 |
| 25.83 | 3.45 | 7.10 |
| 27.17 | 3.28 | 15.50 |
| 28.77 | 3.10 | 5.90 |
| 30.23 | 2.95 | 4.80 |

TABLE 4-continued

| Angle [°2θ] ±0.2° | d-Value[Å] | Relative intensity [%] |
|---|---|---|
| 32.10 | 2.79 | 10.10 |
| 32.48 | 2.75 | 10.40 |

19) The Amorphous Form XIX of Compound 1 Monooxalate

In one embodiment, the form is the amorphous form XIX of compound 1 monooxalate, characterized in that it has an XRPD pattern substantially as shown in FIG. 55.

In some preferred embodiments, it also has the following characteristics:

1) In the TGA plot, there is a weight loss of 3.63±0.2% by weight before 105° C.; and a weight loss of 10.4±0.2% by weight between 105° C. and 242° C.;

2) In the mDSC curve, there is a glassy transition temperature at the midpoint temperature of 100.62±2.0° C.;

3) the TGA plot substantially as shown in FIG. 56; and/or 4) the mDSC curve substantially as shown in FIG. 57.

20) The Amorphous Form XX of Compound 1 Dioxalate

In one embodiment, the form is the amorphous form XX of compound 1 dioxalate, characterized in that it has an XRPD pattern substantially as shown in FIG. 58.

In some preferred embodiments, it also has the following characteristics:

1) In the TGA plot, there is a weight loss of 3.52±0.2% by weight before 122° C.; and a weight loss of 11.6±0.2% by weight between 122° C. and 236° C.;

2) In the mDSC curve, there is a glassy transition temperature at the midpoint temperature of 97.8±2.0° C.;

3) the TGA plot substantially as shown in FIG. 59; and/or 4) the mDSC curve substantially as shown in FIG. 60.

21) The Amorphous Form XXI of Compound 1 Dimaleate

In one embodiment, the form is the amorphous form XXI of compound 1 dimaleate, characterized in that it has an XRPD pattern substantially as shown in FIG. 61.

In some preferred embodiments, it also has the following characteristics:

1) In the TGA plot, there is a weight loss of 2.29±0.2% by weight before 117° C.; and a weight loss of 8.33±0.2% by weight between 117° C. and 216° C.;

2) In the mDSC curve, there is a glassy transition temperature at the midpoint temperature of 142.29±2.0° C.;

3) the TGA plot substantially as shown in FIG. 62; and/or 4) the mDSC curve substantially as shown in FIG. 63.

In one embodiment, 1H-NMR results showed that the molar ratio of the compound 1 to maleic acid in Form XXI was 1:1.90.

22) The Amorphous Form XXII of Compound 1 Ditartrate

In one embodiment, the form is the amorphous form XXII of compound 1 ditartrate, characterized in that it has an XRPD pattern substantially as shown in FIG. 64.

In some preferred embodiments, it also has the following characteristics:

1) In the TGA plot, there is a weight loss of 3.14±0.2% by weight before 127.5° C.; and a weight loss of 15.15±0.2% by weight between 127.5° C. and 272.5° C.;

2) In the mDSC curve, there is a glassy transition temperature at the midpoint temperature of 155.97±2.0° C.;

3) the TGA plot substantially as shown in FIG. 65; and/or 4) the mDSC curve substantially as shown in FIG. 66.

In one embodiment, 1H-NMR results showed that the molar ratio of the compound 1 to tartaric acid was 1:2.02.

23) The Amorphous Form XXIII of Compound 1 Disulfate

In one embodiment, the form is the amorphous form XXIII of compound 1 disulfate, characterized in that it has an XRPD pattern substantially as shown in FIG. 67.

In some preferred embodiments, it has the following characteristics:

1) In the TGA plot, there is a weight loss of 4.77±0.2% by weight before 100° C.;

2) In the mDSC curve, there is a glassy transition temperature at the midpoint temperature of 174.60±2.0° C.;

3) the TGA plot substantially as shown in FIG. 68; and/or 4) the mDSC curve substantially as shown in FIG. 69.

In the second respect, the present invention provides a method for preparing the crystalline forms or amorphous forms of the compound 1 or its salts.

In one embodiment, the present invention provides a method for preparing crystalline form of the compound 1, which comprises the following steps: mixing the compound 1 with solvent, suspending and stirring at room temperature to 50° C., optionally adding seed crystals of corresponding crystalline form, separating the resulting solid and drying, and thereby obtaining the crystalline form of the compound 1.

In the preparation method, the compound 1 can be obtained from a variety of sources, such as commercial purchase or laboratory synthesis. The solvents can be commonly used in laboratory, such as one or more of the water, alkane solvents, alcohol solvents, ketone solvents, ester solvents, aromatic hydrocarbon solvents, halogenated hydrocarbon solvents, nitrile solvents, ether solvents, aliphatic hydrocarbon solvents, polar aprotic solvents such as DMF, DMSO. The mass-volume ratio of the compound 1 to the solvent can be 100 mg: (0.1-10 mL).

In one embodiment, the solvent is selected from IPA/H2O mixed solvent or THF/n-heptane mixed solvent.

In one embodiment, the temperature can be room temperature or 50° C.

In one embodiment, the separation is centrifugal separation; and/or the drying is vacuum drying.

In one embodiment, the present invention provides a method for preparing the amorphous forms of the compound 1 salts, which comprises the following steps: mixing the compound 1 with solvent and acid, suspending and stirring at room temperature −50° C., and isolating the obtained solid, thereby obtaining amorphous forms of the compound 1 salts.

In the preparation method, the compound 1 can be obtained from a variety of sources, such as commercial purchase or laboratory synthesis. The solvents can be commonly used in laboratory, such as one or more of the water, alkane solvents, alcohol solvents, ketone solvents, ester solvents, aromatic hydrocarbon solvents, halogenated hydrocarbon solvents, nitrile solvents, ether solvents, aliphatic hydrocarbon solvents, polar aprotic solvents such as DMF, DMSO. The mass-volume ratio of the compound 1 to the solvent can be 100 mg: (0.1-10 mL).

In one embodiment, the acids can be hydrochloric acid, sulfuric acid, phosphoric acid, methanesulfonic acid, maleic acid, tartaric acid, benzoic acid, succinic acid and acetic acid.

In one embodiment, the temperature can be room temperature or 50° C.

In one embodiment, the separation is centrifugal separation.

In one embodiment, the present invention provides a method for preparing the amorphous forms of the compound 1, which comprises the following steps: mixing the compound 1 with solvent to form solution, and then adding anti-solvent to the solution to separate the resulting solid. Then the amorphous forms of the compound 1 are obtained.

In one embodiment, the solvent is selected from one or more of ethanol, acetone, IPA, 2-MeTHF, dichloromethane, 1,4-dioxane, THF, and DMSO; and/or the anti-solvent is selected from one or more of IPAc, MTBE, heptane, toluene, and water.

In one embodiment, the present invention provides a method for preparing the crystalline form of the salt of the compound 1, which comprises the following steps: mixing the compound 1 with a solvent and an acid, separating the resulting solid and drying, thereby obtaining the crystalline form of the salt of the compound 1; and/or the mass-volume ratio of the compound 1 to the solvent is 100 mg: (0.1-10 mL).

In one embodiment, the solvent is selected from ethanol and acetone;

In one embodiment, wherein the acid is selected from methanesulfonic acid.

In the third aspect, the present invention provides a pharmaceutical composition comprising the above-mentioned crystalline forms or amorphous forms of compound 1 or its salts, and pharmacologically acceptable excipients.

The amount of crystalline forms or amorphous forms of compound 1 or its salts can be a therapeutically effective amount. The pharmacically acceptable excipients can be well known in the art, which in the case of solid formulations include but are not limited to: diluents, adhesives, disintegrants, lubricants, flow aids, release rate control agents, plasticizers, preservatives, antioxidants, etc.

The pharmaceutical compositions can choose the dosage forms suitable for human consumption, such as tablet, capsule, granule, powder, or pill, etc., preferably tablet, capsule, granule, disintegrating tablet, sustained release or controlled release tablet, etc.

The pharmaceutical compositions in the present invention can be prepared by various methods that are well known in the art. One or more of crystalline forms or amorphous forms of the compound 1 or its salts in a therapeutic effective amount can be mixed with one or more of pharmacically acceptable excipients to prepare dosage forms for human consumption, such as tablets, capsules, granules, etc.

The "therapeutically effective amount" is the amount of the compound in the form of the present invention that, when administered to a patient in need, is sufficient to achieve therapeutic effect of a disease state, condition, or disorder. Such amount would be sufficient to elicit the biological or medical response in the tissue system or patient sought by researchers or clinicians.

In the fourth aspect, the present invention provides the use of the crystalline forms or amorphous forms of above mentioned compound 1 or its salts or the use of above mentioned pharmaceutical compositions in the preparation of drugs for the prevention and/or treatment of the disease or condition related to hepatitis virus.

In one embodiment, the disease or condition related to hepatitis virus is a disease or condition related to hepatitis A virus, hepatitis B virus or hepatitis C virus. Preferably, the disease or condition is selected from hepatitis A, hepatitis B, hepatitis C and liver cirrhosis.

The present invention discovers a variety of unreported crystalline forms or amorphous forms of the compound 1 or its salts for the first time, which can serve as an important basis for subsequent drug development, formulation development and production.

BRIEF DESCRIPTION OF THE DRAWINGS

FIG. 64 is an XRPD pattern of Compound 1 ditartrate amorphous Form XXII.

FIG. 65 is a TGA plot of Compound 1 ditartrate amorphous Form XXII

FIG. 66 is a mDSC curve of Compound 1 ditartrate amorphous Form XXII.

DETAILED DESCRIPTION OF THE INVENTION

Examples

Figure 1:
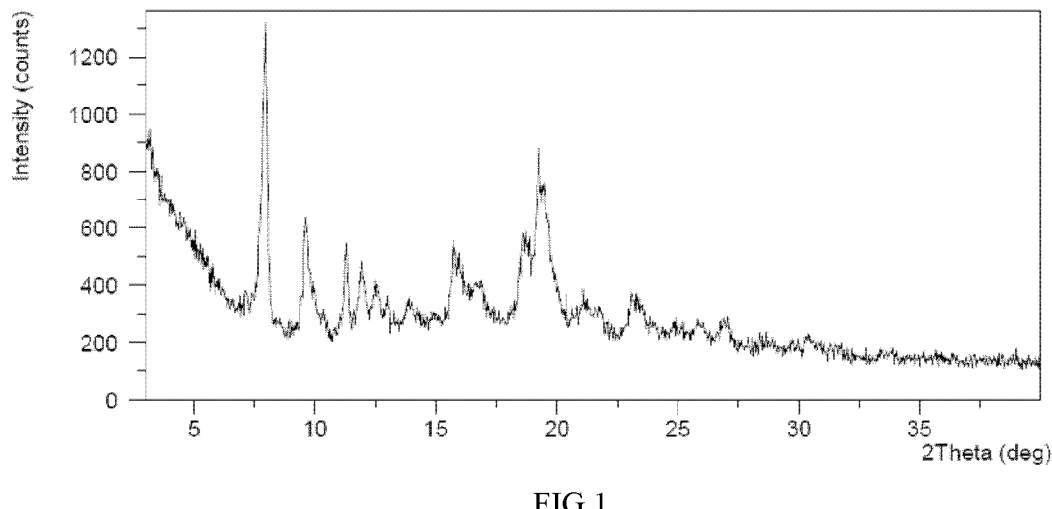
FIG. 1 is an XRPD pattern of Compound 1 crystalline Form I.
Figure 2:
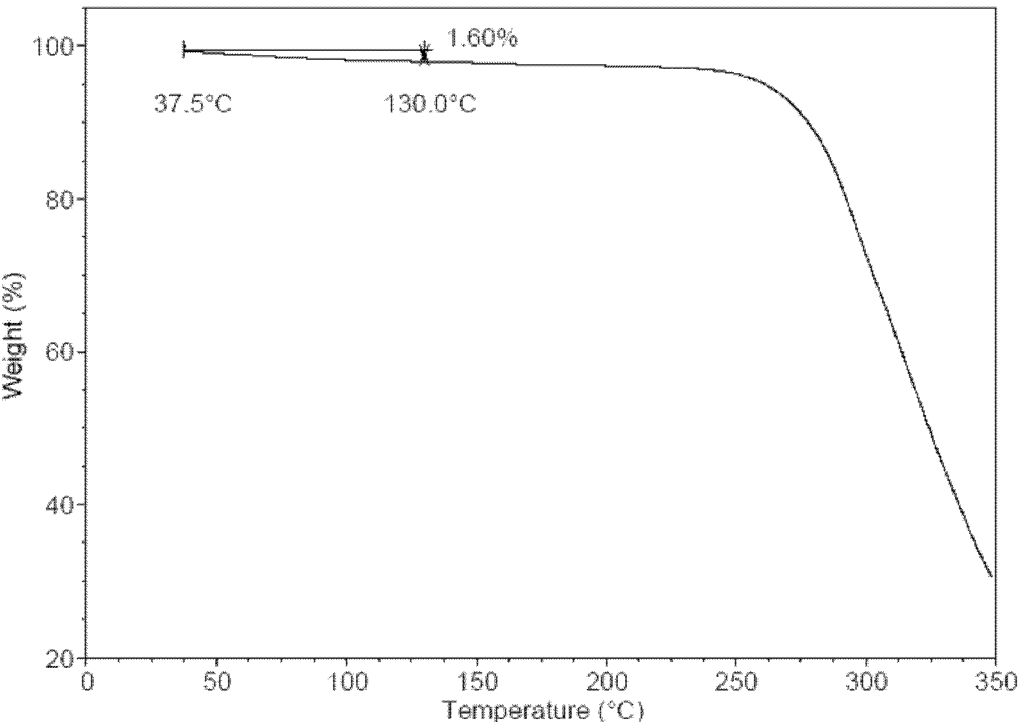
FIG. 2 is a TGA plot of Compound 1 crystalline Form I.
Figure 3:
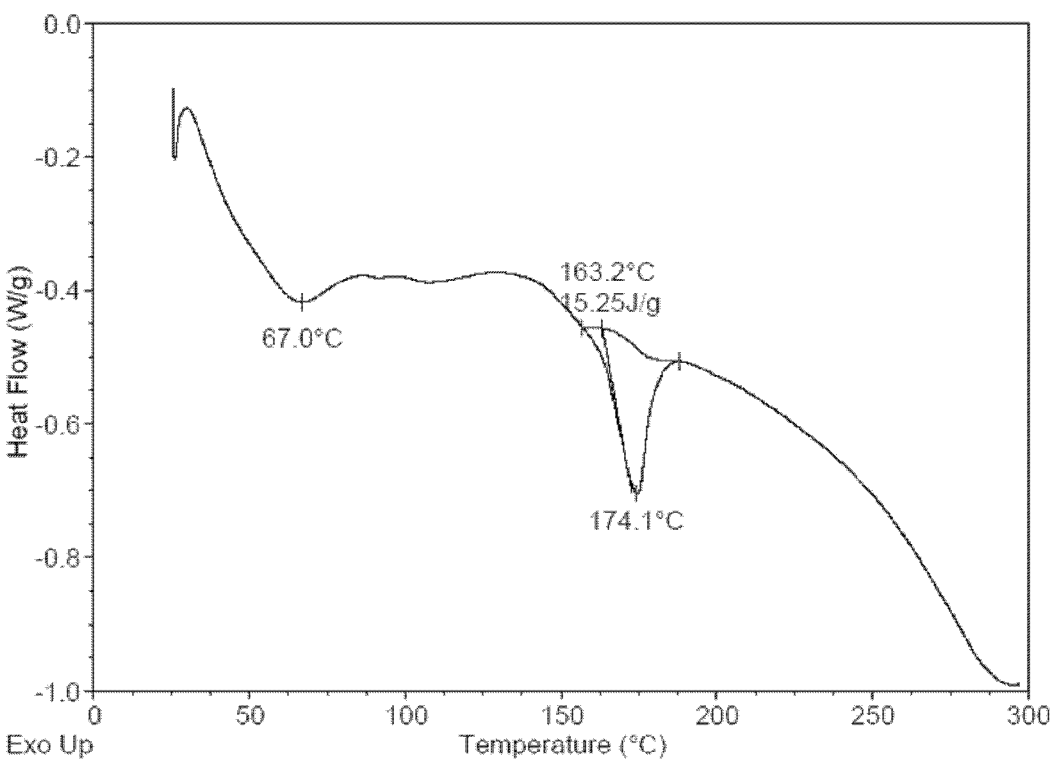
FIG. 3 is a DSC curve of Compound 1 crystalline Form I.
Figure 4:
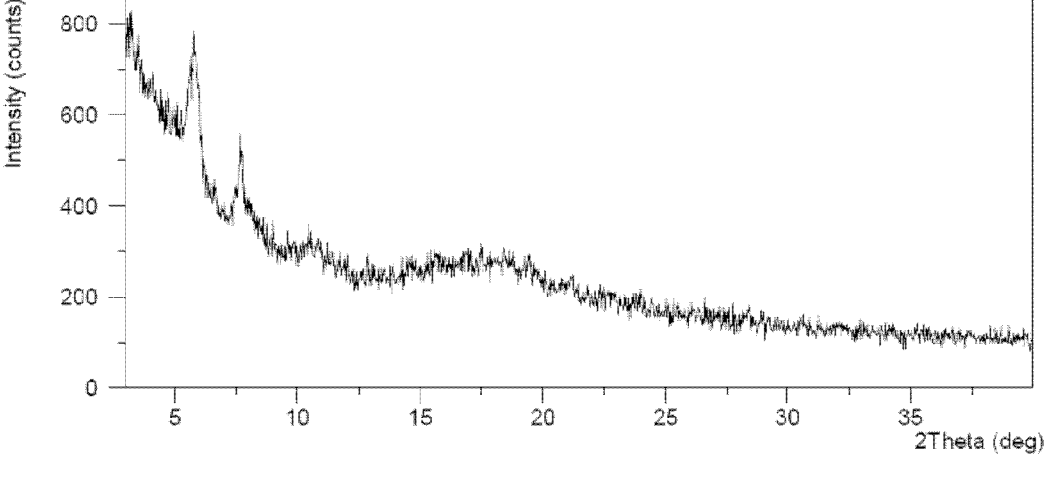
FIG. 4 is an XRPD pattern of Compound 1 crystalline Form II.
Figure 5:
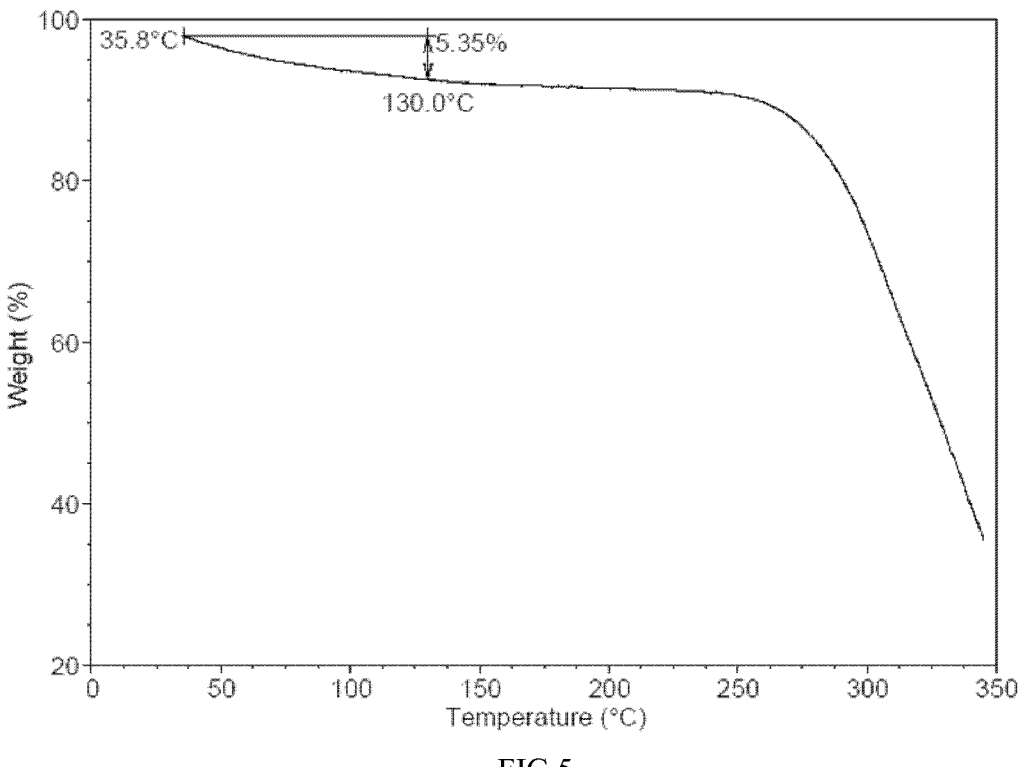
FIG. 5 is a TGA plot of Compound 1 crystalline Form II.
Figure 6:
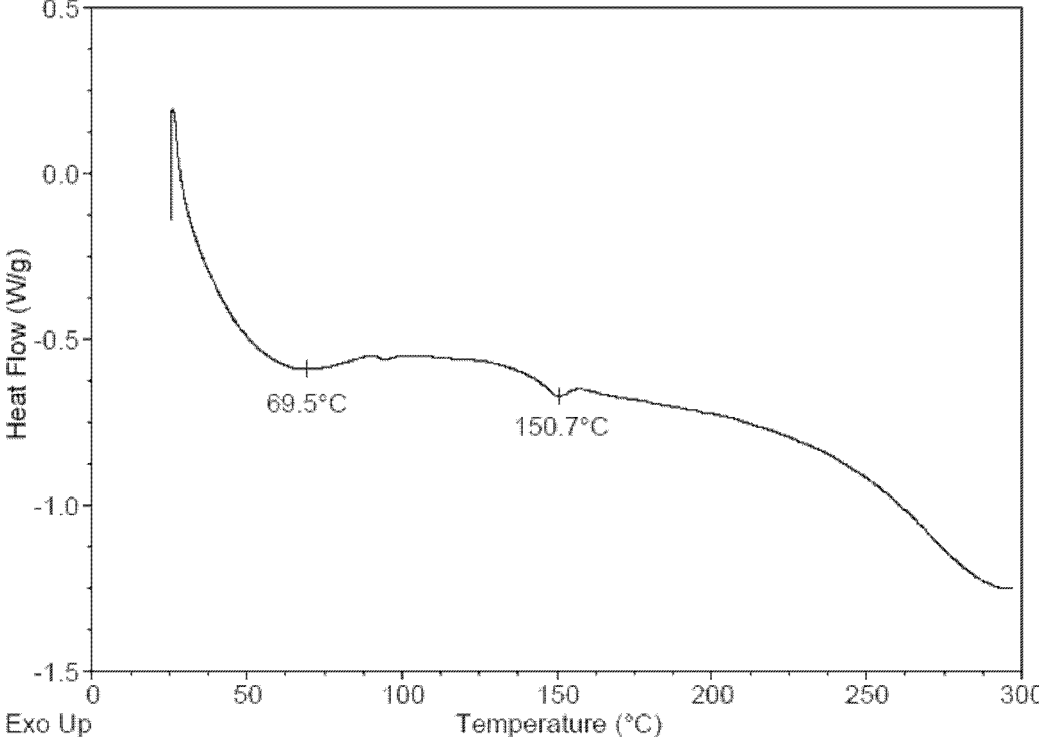
FIG. 6 is a DSC curve of Compound 1 crystalline Form II.
Figure 7:
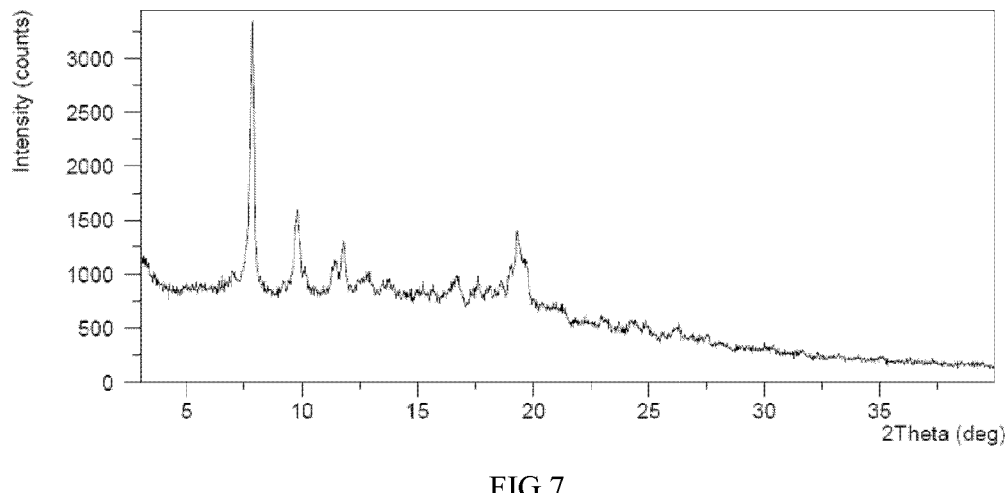
FIG. 7 is an XRPD pattern of Compound 1 crystalline Form III.
Figure 8:
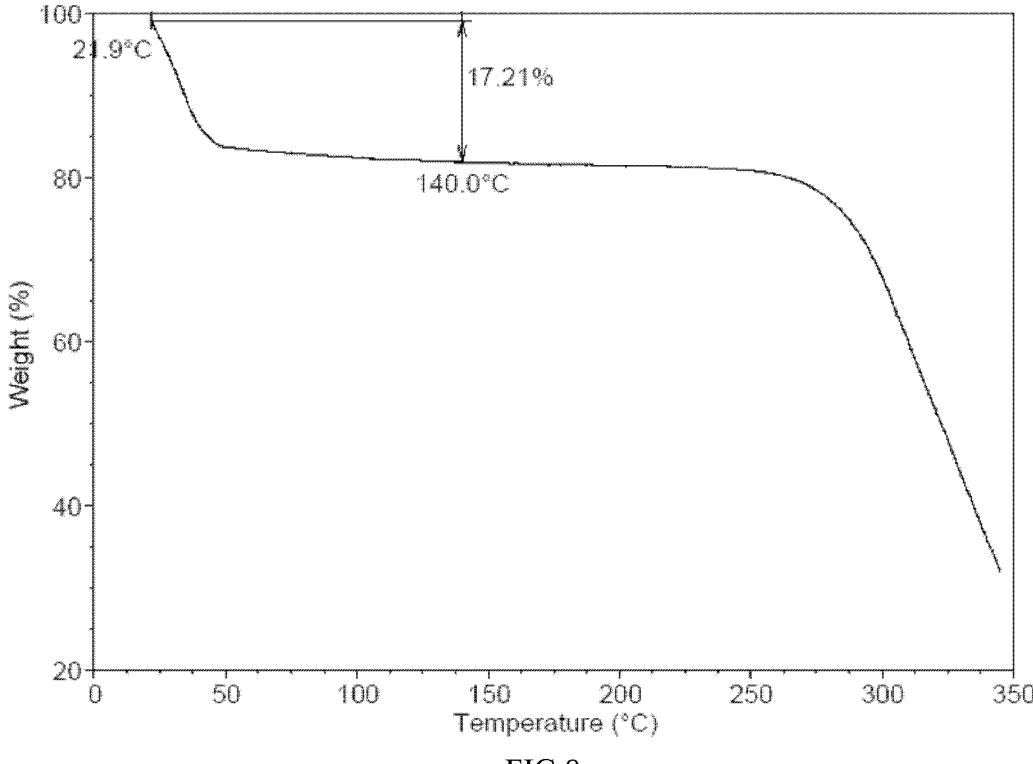
FIG. 8 is a TGA plot of Compound 1 crystalline Form III.
Figure 9:
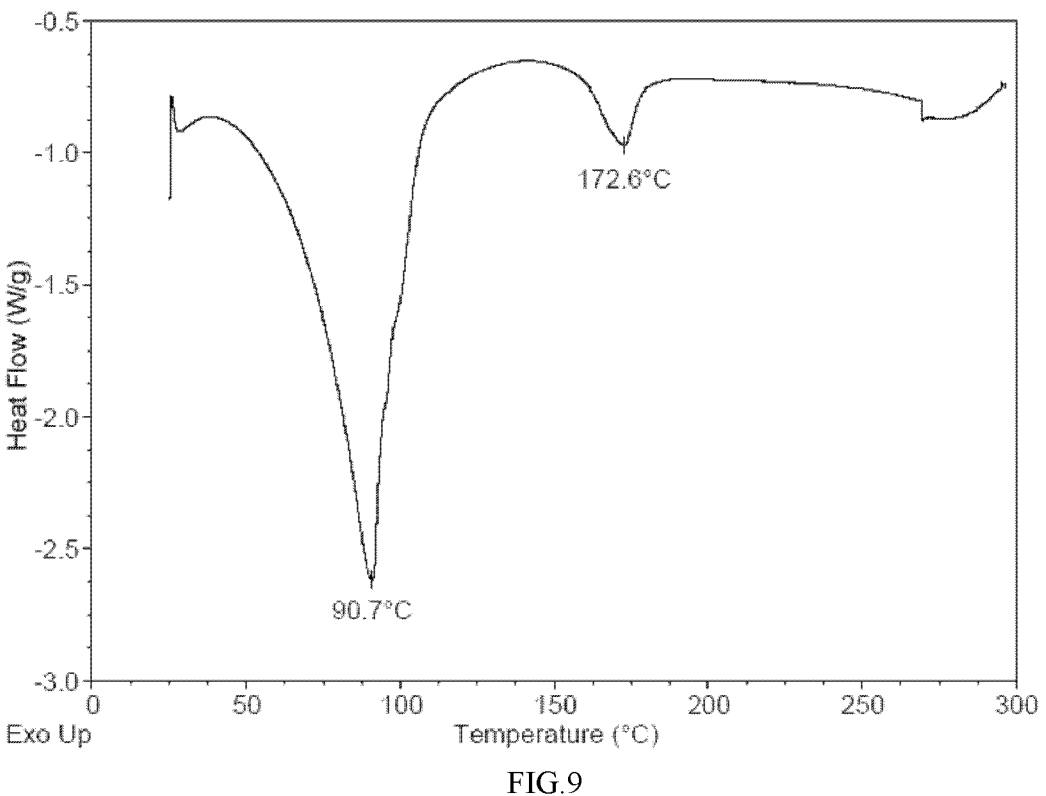
FIG. 9 is a DSC curve of Compound 1 crystalline Form III.

In the following examples, the experimental methods are completed in accordance with conventional conditions or conventional test conditions, and the compounds used in the examples are commercially available or self-made.

Example 1—Screening and Preparation Experiment of the Crystalline Form of the Compound 1

The following different experimental methods were used to screen the possible crystalline forms of the compound 1.

1.1 Anti-Solvent Addition Experiment of Compound 1

A total of 16 anti-solvent addition experiments were set up with different solvents. Approximately 15 mg of the compound 1 was weighed into a 20 mL vial, and the solid was dissolved completely with 0.2-2.0 mL of solvent. The anti-solvent was added dropwise to the clear solution while stirring (1000 rpm) until solids were precipitated, or when the total volume of anti-solvent was added to 15 mL, the sample without solids precipitated was suspended and stirred at 5° C. If there was still no solid precipitation, suspended and stirred at −20° C. The clear sample evaporated at room temperature. The precipitated solids were separated and tested by XRPD. The results are shown in Table 5.

TABLE 5

| Test Number | Solvent | Anti-solvent | Solid Form |
|---|---|---|---|
| 1 | EtOH | IPAc | Amorphous Form* |
| 2 | Acetone | | Amorphous Form* |
| 3 | IPA | MTBE | Amorphous Form* |
| 4 | 2-MeTHF | | Amorphous Form# |
| 5 | DCM | | Amorphous Form |
| 6 | 1,4-dioxane | n-heptane | Amorphous Form* |
| 7 | THF | | Amorphous Form |
| 8 | DCM | | Amorphous Form |
| 9 | IPA | | Amorphous Form |
| 10 | IPA/IPAc(1:9) | | Amorphous Form |
| 11 | Acetone | | Amorphous Form* |
| 12 | IPA | Toluene | Amorphous Form* |
| 13 | DCM | | Amorphous Form* |
| 14 | IPA | H₂O | Amorphous Form |
| 15 | DMSO | | Amorphous Form |
| 16 | 1,4-dioxane | | Amorphous Form* |

Notes:
Amorphous* was obtained by stirring at −20° C., and amorphous# was obtained by stirring at 5° C.

1.2 Slow Evaporation Experiment of Compound 1

A total of 8 slow evaporation tests were set up with different solvent systems. Approximately 15 mg of the compound 1 was weighed and added into a 3-mL vial, 0.2-1.6 mL of solvent was added to dissolve (the undissolved sample was filtered with a 0.45 μm PTFE filter) respectively, and the vial was sealed with Parafilm® sealing film. Pierce 5 pinholes on it, and place it at room temperature to evaporate slowly. The obtained solid was collected for XRPD test. The results are shown in Table 6.

TABLE 6

| Test Number | Solvent | Solid Form |
|---|---|---|
| 1 | MeOH | Amorphous Form |
| 2 | Acetone | Amorphous Form |
| 3 | IPA | Amorphous Form |
| 4 | THF | Amorphous Form |
| 5 | ACN | Amorphous Form |
| 6 | DCM | Amorphous Form |
| 7 | EtOAc | Amorphous Form |
| 8 | 2-MeTHF | Amorphous Form |

1.3 Slow Cooling Experiment of Compound 1

A total of 7 slow cooling tests were set up with different solvent systems. About 15 mg of the compound 1 was weighed and added into a 3-mL vial, 0.6-1.0 mL of solvent was added, stirred and equilibrated at 50° C. for about 2 hours, and then filtered and obtained the supernatant. The obtained supernatant was placed in a biochemical incubator, cooled down from 50° C. to 5° C. at a rate of 0.1° C./min, and then maintain a constant temperature at 5° C. The precipitated solid was collected for XRPD test. Transferred the sample with no solid precipitated to −20° C. and let it stand. If there was still no solid precipitated, transfer to −20° C. for volatilization. The results are shown in Table 7.

TABLE 7

| Test Number | Solvent | Solid Form |
|---|---|---|
| 1 | IPA | Amorphous Form |
| 2 | MIBK | Amorphous Form |
| 3 | EtOAc | Amorphous Form# |
| 4 | IPA/IPAc (1:9) | Amorphous Form* |
| 5 | ACN/Toluene (2:23) | Amorphous Form# |
| 6 | MeOH/MTBE (1:4) | Amorphous Form# |
| 7 | THF/n-heptane (4:1) | Amorphous Form# |

Notes:
Amorphous* was obtained by standing at −20° C., and Amorphous# was obtained by evaporating after standing at −20° C. for 13 days.

1.4 The Slurry and Stirring Experiment of Compound 1 at Room Temperature

About 15 mg of the compound 1 was weighed and added into HPLC glass vials, 0.5 mL of solvent was added, and the resulting turbid liquid was placed under magnetic stirring (1000 rpm) at room temperature. After stirring at room temperature for 5 days, transferred the clear sample to 5° C. After stirring for 20 days at room temperature, the clear sample was transferred to −20° C. and stirred, and the solid was collected by centrifugation (10000 rpm, 2 minutes) for XRPD test. If there was no solid precipitation after stirring, transfer to −20° C. or evaporate at room temperature. The results are shown in Table 8.

TABLE 8

| Test Number | Solvent | Solid Form |
|---|---|---|
| 1 | MIBK | Amorphous Form |
| 2 | MeOH/MTBE (1:9) | Amorphous Form* |
| 3 | MeOH/MTBE (1:19) | Amorphous Form |
| 4 | IPA/IPAc (1:9) | Amorphous Form# |
| 5 | EtOAc | Amorphous Form# |
| 6 | MTBE | Amorphous Form |
| 7 | n-heptane | Amorphous Form |
| 8 | Toluene | Amorphous Form |
| 9 | CHCl₃/n-heptane (1:19) | Amorphous Form |
| 10 | DCM/Toluene (1:19) | Amorphous Form |
| 11 | ACN/IPAc (1:19) | Amorphous Form |
| 12 | THF/n-heptane (3:2) | Crystalline Form II* |
| 13 | THF/n-heptane (2:1) | Amorphous Form |

TABLE 8-continued

| Test Number | Solvent | Solid Form |
|---|---|---|
| 14 | IPAc | Amorphous Form |
| 15 | Acetone/Toluene (2:23) | Amorphous Form+ |
| 16 | IPA | Amorphous Form |
| 17 | H₂O | Amorphous Form |

Notes:

Amorphous* was obtained by stirring at 5° C.; Amorphous# was obtained by evaporating at −20° C.; Amorphous+ was obtained by evaporating at room temperature.

1.5 the Slurry and Stirring Experiment of Compound 1 at 5° C.

Approximately 15 mg of the compound 1 was weighed and added into HPLC glass vial, 0.3 mL of solvent was added, and the resulting suspension was magnetically stirred at 5° C. (1000 rpm). The clarified sample was transferred to −20° C., stirred, and centrifuged (10000 rpm, 2 minutes). The solids were collected for the XRPD test. If there was still no solid precipitation, transfer to −20° C. or evaporate at room temperature. The results are shown in Table 9.

TABLE 9

| Test Number | Solvent | Solid Form |
|---|---|---|
| 1 | EtOAc | Amorphous Form |
| 2 | IPA/IPAc (1:9) | Amorphous Form |
| 3 | IPA | Amorphous Form |
| 4 | MIBK | Amorphous Form |
| 5 | MeOH/MTBE (1:4) | Amorphous Form* |
| 6 | Acetone/Toluene(2:23) | Amorphous Form* |
| 7 | CHCl₃/n-heptane (1:9) | Amorphous Form |
| 8 | THF/n-heptane (4:1) | Amorphous Form# |

Notes:

Amorphous* was obtained by evaporating at −20° C. or room temperature, and amorphous# was obtained by stirring at −20° C.

1.6 The Slurry and Stirring Experiment of Compound 1 at 50° C.

15 mg of the compound 1 was weighed and added into HPLC glass vial, 0.3 mL of solvent was added, the resulting suspension was magnetically stirred at 50° C. (1000 rpm), the clear sample was transferred to room temperature and stirred, if there was still no solid precipitation, then transferred at 5° C. or −20° C. and stirred, centrifugated (10000 rpm, 3 minutes) to collect the solid for XRPD test. In the end, samples that were still clear were transferred to −20° C. to evaporate, and the results are shown in Table 10.

TABLE 10

| Test Number | Solvent | Solid Form |
|---|---|---|
| 1 | MeOH/MTBE (1:19) | Amorphous Form |
| 2 | MeOH/MTBE (1:9) | Amorphous Form |
| 3 | 1,4-dioxane/n-heptane(1:19) | Amorphous Form |
| 4 | n-heptane | Amorphous Form |
| 5 | Toluene | Amorphous Form |
| 6 | H2O | Amorphous Form |
| 7 | IPA/H₂O (1:9) | Crystalline Form I |
| 8 | MTBE | Amorphous Form |
| 9 | IPAc | Amorphous Form |
| 10 | MIBK | Amorphous Form |
| 11 | THF/n-heptane (3:2) | Crystalline Form II* |
| 12 | EtOAc | Amorphous Form* |
| 13 | IPA/H₂O (1:1) | Amorphous Form# |
| 14 | IPA/IPAc (1:9) | Amorphous Form* |

Notes:

Amorphous* was obtained by stirring at 5° C., and amorphous# was obtained by stirring at −20° C.

1.7 Gas-Solid Permeation Experiment of Compound 1

A total of 9 gas-solid diffusion tests were set up with different solvents. 15 mg of the compound 1 was weighed and added into a 3 mL vial, about 2 mL of solvent was added into the 20 mL vial, the 3 mL vial was placed open in the 20 mL vial, and then the 20 mL vial was sealed. After standing at room temperature for 19 days, the solids were collected for XRPD testing. If the sample was dissolved, the solid was collected by evaporating at room temperature. The results are shown in Table 11.

TABLE 11

| Test Number | Solvent | Solid Form |
|---|---|---|
| 1 | MIBK | Amorphous Form |
| 2 | IPAc | Amorphous Form |
| 3 | MTBE | Amorphous Form |
| 4 | n-heptane | Amorphous Form |
| 5 | Toluene | Amorphous Form |
| 6 | H₂O | Amorphous Form |
| 7 | IPA | Amorphous Form* |
| 8 | CHCl₃ | Amorphous Form* |
| 9 | DMSO | Amorphous Form* |

Notes:

Amorphous* was obtained by evaporating at room temperature.

1.8 Gas-Liquid Diffusion Experiment of Compound 1

A total of 13 gas-liquid diffusion tests were set up with different solvents. About 15 mg of the compound 1 was weighed and added into a 3 mL vial, 0.2~1.4 mL of solvent was added to dissolve it (0.45 μm PTFE filter for undissolved solid), Another 20 mL vial was taken and about 3 mL of antisolvent was added into it, After placing the 3 mL vial containing the clear liquid (open) into the 20 mL vial, the 20 mL vial was sealed and allowed to stand at room temperature. Collect solids and perform XRPD testing. If the sample was dissolved, evaporated at room temperature and perform XRPD test for collected solids. The results are shown in Table 12.

TABLE 12

| Test Number | Solvent | Anti-solvent | Solid Form |
|---|---|---|---|
| 1 | IPA | n-heptane | Amorphous Form* |
| 2 | Acetone | | Amorphous Form |
| 3 | 2-MeTHF | | Amorphous Form |
| 4 | DCM | | Amorphous Form |
| 5 | ACN | | Amorphous Form |
| 6 | 1,4-dioxane | | Amorphous Form |
| 7 | CHCl₃ | Toluene | Amorphous Form |
| 8 | Acetone | | Amorphous Form |
| 9 | IPA/IPAc (1:9) | MTBE | Amorphous Form |
| 10 | ACN | | Amorphous Form* |
| 11 | IPA | H₂O | Amorphous Form |
| 12 | THF | | Amorphous Form |
| 13 | Acetone | | Amorphous Form |

Notes:

Amorphous* was obtained by evaporating at room temperature.

1.9 Polymorph Screening Test of Compound 1 Dimethylsulfonate 40 mg of the compound was taken and added into a 2 mL glass bottle, a stir bar and then 400 μL of solvent were added (as shown in Table 13 below). If the sample was dissolved, let it stand at room temperature and evaporated. Other suspensions were stirring for 2 days at 40° C., quickly centrifuge (6000 rpm, 10 min), and the remaining solid was taken out and dried in a vacuum drying oven (−0.1 Mpa, 25° C.). The results are shown in Table 13.

TABLE 13

| Test number | Solvent | XRPD results |
|---|---|---|
| — | Initial Crystalline Form | Crystalline Form XVIII |
| 1 | Ethanol | Crystalline Form XVIII |
| 2 | Isopropanol | Crystalline Form XVIII |
| 3 | Acetonitrile | Crystalline Form XVIII |
| 4 | Ethyl acetate | Crystalline Form XVIII |
| 5 | Isopropyl acetate | Crystalline Form XVIII |
| 6 | Tert-butyl methyl ether | Crystalline Form XVIII |
| 7 | Tetrahydrofuran | Crystalline Form XVIII |
| 8 | Methyltetrahydrofuran | Crystalline Form XVIII |
| 9 | Dichloromethane | Crystalline Form XVIII |
| 10 | N-heptane | Crystalline Form XVIII |
| 11 | Acetone/ethyl acetate = 2/1 | Crystalline Form XVIII |

1.10 Stability Test of Salts of Compound 1

30 mg of the compound was weighed and added into an 8 mL glass bottle, and then was placed under the condition of room temperature (25° C., closed), high humidity (room temperature/75% RH, open) and light (25° C. closed, white light: 5000 Lux, ultraviolet 282 μW/cm2). samples were taken on the 5th, 10th, and 30th day for detection (HPLC, XRD).

TABLE 14

| Sample | Test conditions | Time point (day) | TRS (%) | XPRD |
|---|---|---|---|---|
| compound 1 dihydrochloride amorphous form V | Initial sample | 0 | 0.73 | Amorphous |
| | 25° C. closed | 5 | 0.72 | Amorphous |
| | | 10 | 0.77 | Amorphous |
| | | 30 | 0.83 | Amorphous |
| | 25° C./75% RH open | 5 | 0.81 | Amorphous |
| | | 10 | 0.77 | Amorphous |
| | | 30 | 0.79 | Amorphous |
| | Illumination 5K lux closed | 5 | 1.81 | Amorphous |
| | | 10 | 2.54 | Amorphous |
| compound 1 disulfate amorphous form XXIII | Initial sample | 0 | 1.96 | Amorphous |
| | 25° C. | 5 | 2.45 | Amorphous |
| | | 10 | 2.72 | Amorphous |
| | | 30 | 4.83 | Amorphous |
| | 25° C./75% RH | 5 | 2.69 | Amorphous |
| | | 10 | 3.14 | Amorphous |
| | | 30 | 5.13 | Amorphous |
| | illumination 5K lux | 5 | 3.66 | Amorphous |
| | | 10 | 5.50 | Amorphous |
| Compound 1 dimethanesulfonate crystalline Form XVIII | Initial sample | 0 | 2.44 | Crystalline Form XVIII |
| | 25° C. | 5 | 2.51 | Crystalline Form XVIII |
| | | 10 | 2.57 | Crystalline Form XVIII |
| | | 30 | 2.55 | Crystalline Form XVIII |
| | illumination 5K lux | 5 | 2.63 | Crystalline Form XVIII |
| | | 10 | 2.64 | Crystalline Form XVIII |
| Compound 1 di-p-toluenesulfonate amorphous Form XVI. | Initial sample | 0 | 1.66 | Amorphous |
| | 25° C. | 5 | 1.66 | Amorphous |
| | | 10 | 1.71 | Amorphous |
| | | 30 | 1.80 | Amorphous |
| | 25° C./75% RH | 5 | 1.56 | Amorphous |
| | | 10 | 1.66 | Amorphous |
| | | 30 | 1.88 | Amorphous |
| | illumination 5K lux | 5 | 1.89 | Amorphous |
| | | 10 | 2.40 | Amorphous |

Example 2: The Preparation Method of Crystalline Form I of Compound 1

150 mg compound 1 was weighed and added in 5.0 mL of mixed solvent IPA/H2O (1:9, v/v), suspended and stirred at 50° C. for 5 days. After centrifugation, the solid was dried under vacuum at room temperature for 1 day, and about 80 mg solid was taken out and dried under vacuum at 50° C. for 2 hours.

Example 3: The Preparation Method of Crystalline Form II of Compound 1

150 mg compound 1 was weighed and added in 5.0 mL mixed solvent THF/n-heptane (3:2, v/v), suspended and stirred at room temperature for 3 days, transferred to 50° C. and suspended and stirred for 2 days, about 3 mg of the seed crystals of crystalline form II obtained in the above screening test were added, then suspended and stirred at 50° C. for 2 days, centrifuged, and the solid was dried under vacuum at room temperature for 1 day.

Example 4: The Preparation Method of Crystalline Form III of Compound 1

150 mg of the compound 1 was weighed and added in 5.0 mL of mixed solvent IPA/H2O (1:9, v/v), suspended and stirred at 50° C. for 5 days. After centrifugation, the solid was dried under vacuum at room temperature for 4 hours.

Example 5: The Preparation Method of Amorphous Form IV of Compound 1 Monohydrochloride 15 mg of the compound 1 was weighed and added into an HPLC vial, 0.5 mL of solvent MIBK was added, and 1.1 μL of concentrated hydrochloric acid was added, suspended at room temperature and stirred for 3 days, and centrifuged.

Example 6: The Preparation Method of Amorphous Form V of Compound 1 Dihydrochloride 15 mg of the compound 1 was weighed and added into an HPLC vial, 0.5 mL of solvent EtOAc was added, 2.2 μL of concentrated hydrochloric acid was added, suspended and stirred at room temperature for 3 days, and centrifuged.

Example 7: The Preparation Method of Amorphous Form VI of Compound 1 Sulfate 15 mg of the compound 1 was weighed and added into an HPLC vial, 0.5 mL of mixed solvent MeOH/MTBE (1:9, v/v) was added, 0.8 μL of concentrated sulfuric acid was added, suspended and stirred at room temperature for 3 days, and centrifuged.

Example 8: The Preparation Method of Amorphous Form VII of Compound 1 Phosphate 15.0 mg of the compound 1 was weighed and added into an HPLC vial, 0.5 mL of mixed solvent MeOH/MTBE (1:9, v/v) was added, 0.86 μL of concentrated phosphoric acid was added, suspended and stirred at room temperature for 3 days, and centrifuged.

Example 9: The Preparation Method of Amorphous Form VIII of Compound 1 Mesylate 15 mg of the compound 1 was weighed and added into an HPLC vial, 0.5 mL of solvent MIBK was added, 0.83 μL of methanesulfonic acid was added, suspended and stirred at room temperature for 3 days, and centrifuged.

Example 10: The Preparation Method of Amorphous Form IX of Compound 1 Maleate 15 mg of the compound 1 was weighed and added into an HPLC vial, 0.5 mL of mixed solvent MeOH/MTBE (1:9, v/v) was added, 1.6 mg of maleic acid was added, suspended and stirred at room temperature for 3 days, and centrifuged.

Example 11: The Preparation Method of Amorphous Form X of Compound 1 Tartrate 15.0 mg of the compound 1 was weighed and added into an HPLC vial, 0.5 mL of solvent MIBK was added, 2.1 mg of tartaric acid was added, suspended and stirred at room temperature for 3 days, and centrifuged.

Example 12: The Preparation Method of Amorphous Form XI of Compound 1 Benzoate 15.0 mg of the compound 1 was weighed into an HPLC vial, 0.5 mL of mixed solvent MeOH/MTBE (1:9, v/v) was added, 1.6 mg of benzoic acid was added, suspended and stirred at room temperature for 3 days, and centrifuged.

Example 13: The Preparation Method of Amorphous Form XII of Compound 1 Succinate 15.0 mg of the compound 1 was weighed and added into an HPLC vial, 0.5 mL of solvent MIBK was added, 1.6 mg of succinic acid was added, suspended and stirred at room temperature for 3 days, and centrifuged.

Example 14: The Preparation Method of Amorphous Form XIII of Compound 1 Acetate 15.0 mg of the compound 1 was weighed and added into an HPLC vial, 0.5 mL of solvent MIBK was added, 0.6 μL of glacial acetic acid was added, suspended and stirred at room temperature for 3 days, and centrifuged.

Example 15: The Preparation Method of Amorphous Form XIV of Compound 1

About 15 mg of the compound 1 was weighed and added into a 20 mL vial, then the solid was dissolved completely with 0.2-2.0 mL of EtOH. IPAc was added dropwise to the clear solution while stirring (1000 rpm) until solid precipitated, and if there is no solid precipitation, suspended and stirred at 5° C. If there is still no solid precipitation, transferred to −20° C. for suspension and stirring. The clear sample evaporated at room temperature. Then the precipitated solid was separated.

Example 16—the Preparation Method of Amorphous Form XV of the Compound 1 Mono-p-Toluenesulfonate 200 mg of the compound 1 was weighed and added into a 20 mL glass bottle, a stir bar and 2 mL of acetone were added, and then 0.19 mL of 1M p-toluenesulfonic acid in ethanol was added to dissolve the sample, the sample directly turned into oil. After stirring for 2 days, no solids were precipitated. The sample solution evaporated. The remaining solids were taken out and dried in a vacuum drying oven (−0.1 Mpa, 25° C.).

Example 17—the Preparation Method of Amorphous Form XVI of the Compound 1 Di-p-Toluenesulfonate 1000 mg of the compound 1 was weighed and added into a 40 mL glass bottle, a stir bar and 20 mL of acetone were added, and then 1.9 mL of 1M p-toluenesulfonic acid in ethanol was added, the sample directly turned into oil. The n-heptane was added. No solids were precipitated. After stirring for 2 days, the sample solution was concentrated, and the remaining solid was dried in a vacuum drying oven (−0.1 Mpa, 25° C.).

Example 18—the Preparation Method of Amorphous Form XVII of Compound 1 Diphosphate 1000 mg of the compound 1 was weighed and added into a 40 mL glass bottle, a stir bar and 20 mL of acetone were added, and then 1.9 mL of 1M phosphoric acid in ethanol was added, solids were precipitated. After stirring for 2 days, centrifugated (6000 rpm 10 min), the residual solids was taken out and dried in a vacuum drying oven (−0.1 Mpa, 25° C.).

Example 19—the Preparation Method of Crystalline Form XVIII of the Compound 1 Dimethylsulfonate 1000 mg of the compound 1 was weighed and added into a 40 mL glass bottle, a stir bar and 20 mL of acetone were added, and then 1.9 mL of 1M methanesulfonic acid in ethanol was added, the solid was immediately precipitated. After stirring for 2 days, centrifugated (6000 rpm 10 min), the remaining solids was taken out and dried in a vacuum drying oven (−0.1 Mpa, 25° C.).

Example 20—the Preparation Method of Amorphous Form XIX Compound 1 Monooxalate 200 mg of the compound 1 was weighed and added into a 40 mL glass bottle, a stir bar and 20 mL of acetone were added, and then 1.9 mL of 1M oxalic acid in ethanol was added. Solids were precipitated. After stirring for 2 days, centrifugated (6000 rpm. 10 min), the residual solids was taken out and dried in a vacuum drying oven (−0.1 Mpa, 25° C.).

Example 21—the Preparation Method of Amorphous Form XX of Compound 1 Dioxalate 1000 mg of the compound 1 was weighed and added into a 40 mL glass bottle, a stir bar and 20 mL of acetone were added, and then 1.9 mL of 1M oxalic acid in ethanol was added. Solids were precipitated. After stirring for 2 days, centrifugated (6000 rpm. 10 min), the residual solids were taken out and dried in a vacuum drying oven (−0.1 Mpa, 25° C.).

Example 22—the Preparation Method of the Amorphous Form XXI of the Compound 1 Dimaleate 1000 mg of the compound 1 was weighed and added into a 40 mL glass bottle, a stir bar and 20 mL of acetone were added, and then 1.9 mL of 1M maleic acid in ethanol was added. No solid precipitated. The anti-solvent n-heptane was added, there was still no precipitation. After stirring for 2 days, the sample solution was directly concentrated, and the remaining solids was dried in a vacuum drying oven (−0.1 Mpa, 25° C.).

Example 23—the Preparation Method of Amorphous Form XXII of Compound 1 Ditartrate 1000 mg of the compound 1 was weighed and added into a 40 mL glass bottle, a stir bar and 20 mL of acetone were added, and then 1.9 mL of 1M tartaric acid in ethanol was added. Solids were precipitated. After stirring for 2 days, centrifugated (6000 rpm 10 min), the remaining solids were taken out and dried in a vacuum drying oven (−0.1 Mpa, 25° C.).

Example 24—the Preparation Method of Amorphous Form XXIII of Compound 1 Disulfate 1000 mg of the compound 1 was weighed and added into a 40 mL glass bottle, a stir bar and 20 mL of acetone were added, and then 1.9 mL of 1M sulfuric acid in ethanol was added. The sample directly turned into oil. The n-heptane was added, there was still no precipitation. After stirring for 2 days, the sample solution was concentrated, and the remaining solids were dried in a vacuum drying oven (−0.1 Mpa, 25° C.).

Example 25—the DVS Test of Compound 1 Solid Form V/XIV/XVIII

About 10 mg of the solid form of the compound 1 was taken for dynamic water adsorption (DVS) test. The conclusions are described in Table 15 below:

TABLE 15

| Sample | XRPD after DVS |
| --- | --- |
| XIV | No change |
| V | No change |
| XVIII | No change |

Example 26: Identification and Characterization of Various Forms of Compound 1

The used instruments and their parameters are described as follows:
1. XRPD X-Ray Powder Diffraction
X-ray powder diffraction analyzer (PANalytacal)

| Parameters | Instruments |
| --- | --- |
| X rays | X' Pert3 Cu, Kα, Kα1 (Å): 1.540598, Kα2 (Å): 1.544426 Kα2/Kα1 intensity ratio: 0.50 |
| Setting of X-ray tube | 45 kV, 40 mA |
| Divergence slit | 1/8° |
| Scan patterns | Continuous |
| Scanning range (2θ) | 3°-40° |
| Scanning time per step (s) | 46.665 |
| Scanning step size (2θ) | 0.0263° |
| Test Time | ~5 min |

2. TGA Thermogravimetric Analysis and DSC Differential Scanning Calorimetry

TA Q500/5000 thermogravimetric analyzer and TA Q200/2000 differential scanning calorimeter

| Parameter | TGA | DSC |
| --- | --- | --- |
| Method | Linear temperature | Linear temperature |
| Sample plate | Platinum plate, open | Aluminum plate, gland |
| Temperature range | Room temperature-set the end temperature | 25° C.- set the end temperature |
| Scanning rate (° C./min) | 10 | 10 |
| Shielding gas | Nitrogen | Nitrogen |

3. mDSC—Modulated Differential Scanning Calorimetry

| Parameter | Set value |
| --- | --- |
| Test mode | Conventional mDSC |
| Amplitude (° C.) | 1.0 |
| Modulation period (sec.) | 60 |
| Scanning rate (° C./Minute) | 3.0 |
| Shielding gas | Nitrogen |

4. IC—Ion Chromatography

| Parameter | Ion Chromatography (Thermo ICS1100) |
| --- | --- |
| chromatographic column | IonPac AS18 Analytical Column (4 × 250 mm) |
| Mobile phase | 25 mM NaOH |
| Injection volume | 25 μL |
| Flow rate | 1.0 mL/min |
| Cell temperature | 35° C. |
| Column temperature | 35° C. |
| Currrent | 80 mA |
| Run time | $Cl^-$: 6.0 min; $PO_4^{3-}$: 12.0 min; $SO_4^{2-}$: 8.0 min |

Figure 69:
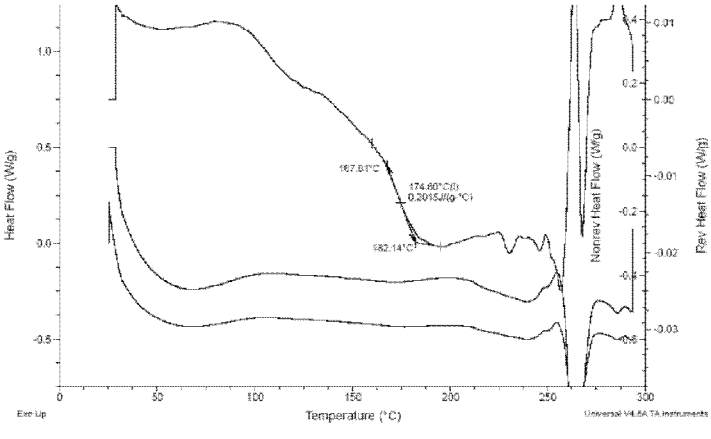
FIG. 69 is a mDSC curve of Compound 1 disulfate amorphous Form XXIII.

For the identification and characterization results of the above XPRD, TGA, DSC, mDSC, etc., please refer to FIG. 1-69, Table 1-4 and related text description.

Each reference, including all patents, patent applications and publications referenced in this application, is incorporated herein by reference in its entirety as if each of them is incorporated separately. In addition, it is understood that in the teaching of the present invention, the technicians in the art may make certain changes or modifications to the present invention and that these equivalents will remain within the scope of the present invention as limited by the claims appended to the application.

What is claimed is:

1. A crystalline or amorphous form of compound 1:

(compound 1)

25

Figure 40:
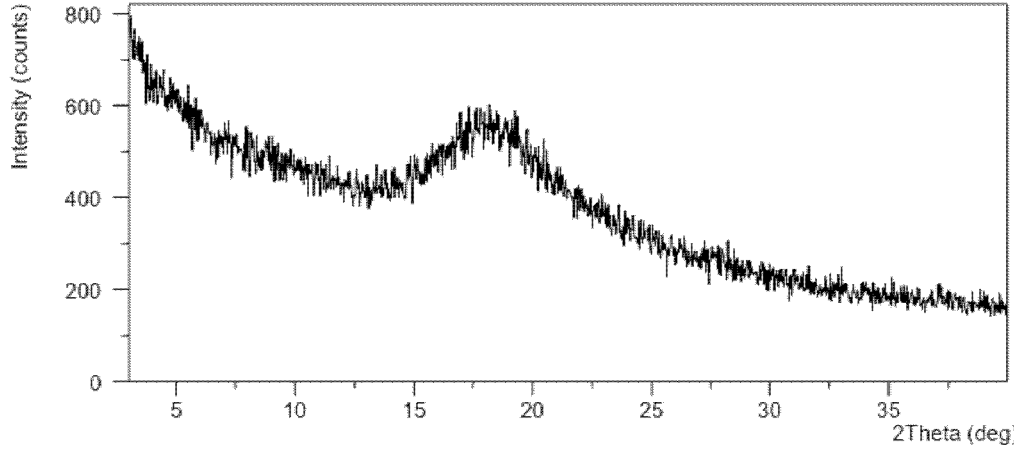
FIG. 40 is an XRPD pattern of Compound 1 amorphous Form XIV.
Figure 41:
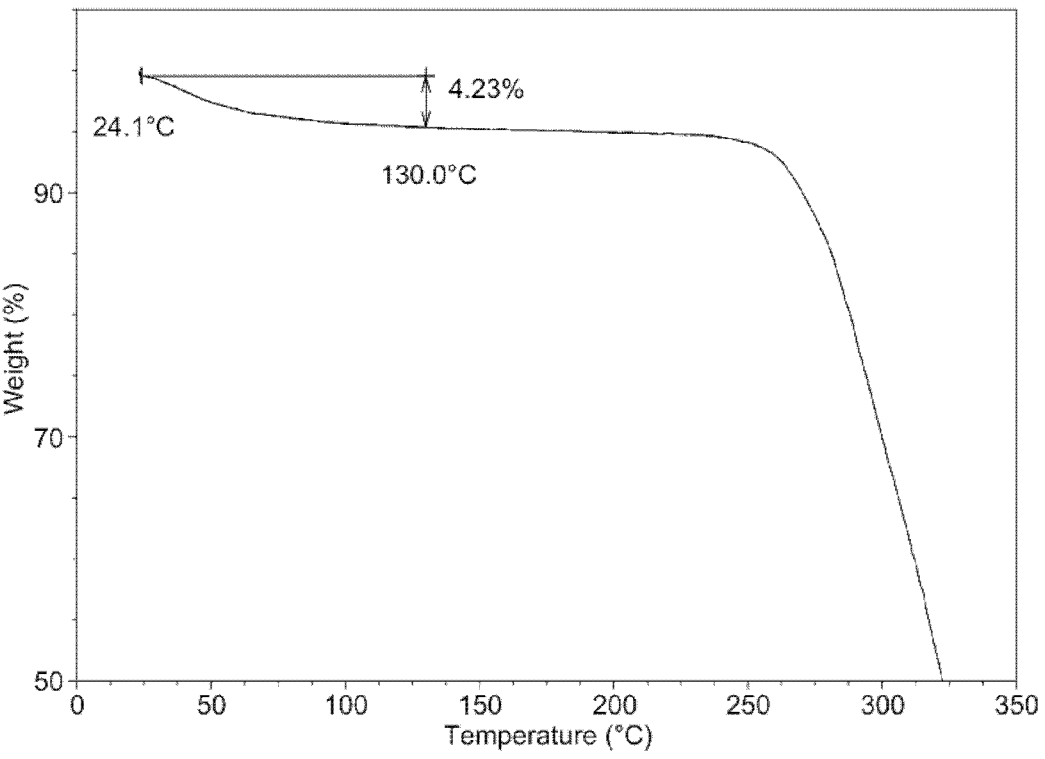
FIG. 41 is a TGA plot of Compound 1 amorphous Form XIV
Figure 42:
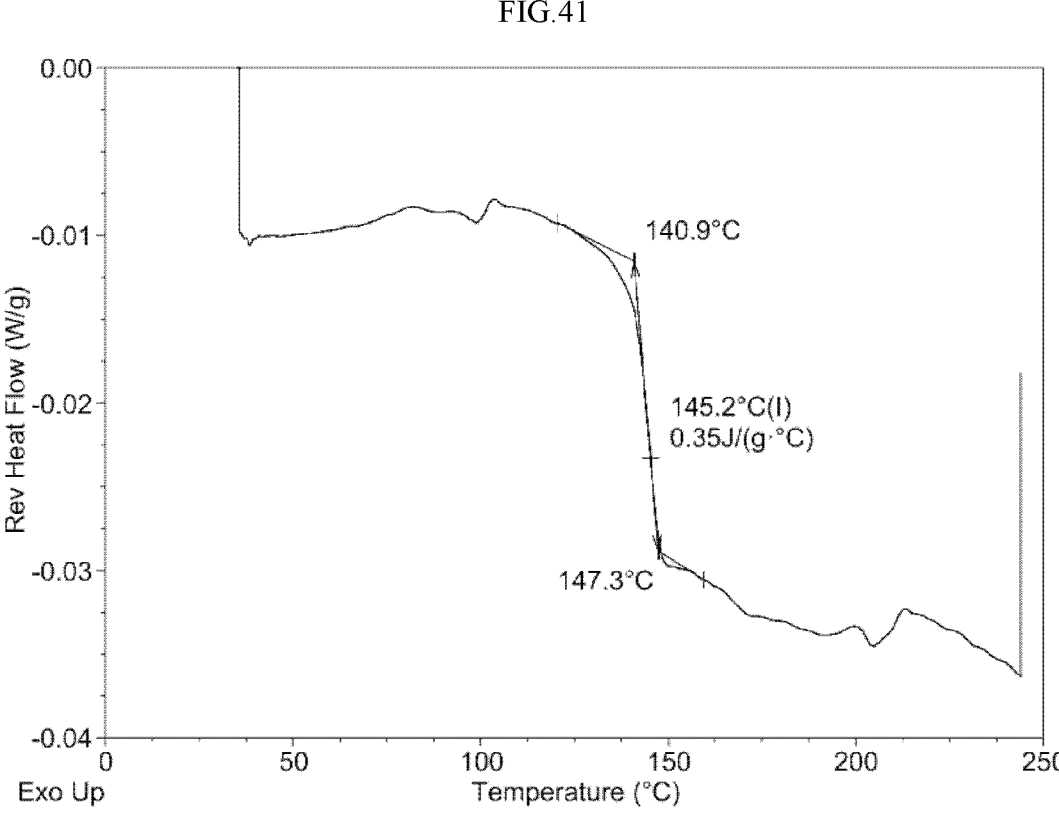
FIG. 42 is a mDSC curve of Compound 1 amorphous Form XIV.

-continued wherein the crystalline or amorphous form of compound 1 is crystalline form I characterized by an X-ray powder diffraction pattern which comprises peaks at 7.93±0.2°, 9.60±0.2°, 11.27±0.2°, 15.73±0.2°, 18.63±0.2°, and 19.22±0.2° in 2θ; and optionally has one or more peaks at 11.92±0.2°, 12.52±0.2°, and 16.72±0.2° in 2θ; or crystalline form II characterized by an X-ray powder diffraction pattern which comprises peaks at 5.80±0.2° and 7.68±0.2° in 2θ; or crystalline form III characterized by an X-ray powder diffraction pattern which comprises peaks at 7.83±0.2°, 9.78±0.2°, 11.78±0.2°, 19.32±0.2°, and 19.68±0.2° in 2θ; or amorphous form XIV characterized by an X-ray powder diffraction pattern as shown in FIG. 40, and optionally has the following characteristics:

1) In a TGA plot, there is a weight loss of 4.2±0.2% by weight before 130° C.;

2) In a mDSC curve, there is a glassy transition temperature at the midpoint temperature of 145.2±2.0° C.;

3) a TGA plot as shown in FIG. 41; and/or 4) a mDSC curve as shown in FIG. 42.

2. The form according to claim 1, wherein the form is amorphous form XIV characterized by an X-ray powder diffraction pattern as shown in FIG. 40, and optionally has the following characteristics:

1) In the TGA plot, there is a weight loss of 4.2±0.2% by weight before 130° C.;

2) In the mDSC curve, there is a glassy transition temperature at the midpoint temperature of 145.2±2.0° C.;

3) the TGA plot as shown in FIG. 41; and/or 4) the mDSC curve as shown in FIG. 42.

3. A method for preparing the amorphous form XIV of the compound 1 according to claim 2, which comprises the following steps:

26 mixing the compound 1 with a solvent to form a solution, adding an anti-solvent to the solution to obtain a solid, and separating the obtained solid, which is an amorphous form XIV of compound 1 wherein the solvent is optionally selected from one or more of ethanol, acetone, IPA, 2-MeTHF, dichloromethane, 1,4-dioxane, THF, DMSO and/or the anti-solvent is selected from one or more of IPAc, MTBE, heptane, toluene, and water.

4. A method for preparing the crystalline form of compound 1 according to claim 1, comprising:

mixing compound 1 with a solvent, suspending and stirring at room temperature at −50° C. to obtain a solid, optionally adding a seed crystal of the corresponding crystalline form, and separating and drying the obtained solid which is a crystalline form of compound 1;

wherein the mass-volume ratio of compound 1 to the solvent is optionally 100 mg: (0.1-10 mL).

5. The preparation method according to claim 4, wherein the solvent is selected from a mixed solvent of IPA/H₂O or a mixed solvent of THF/n-heptane.

6. A pharmaceutical composition comprising the crystalline or amorphous form of compound 1 according to claim 1 and one or more pharmaceutically acceptable excipients.

Figure 10:
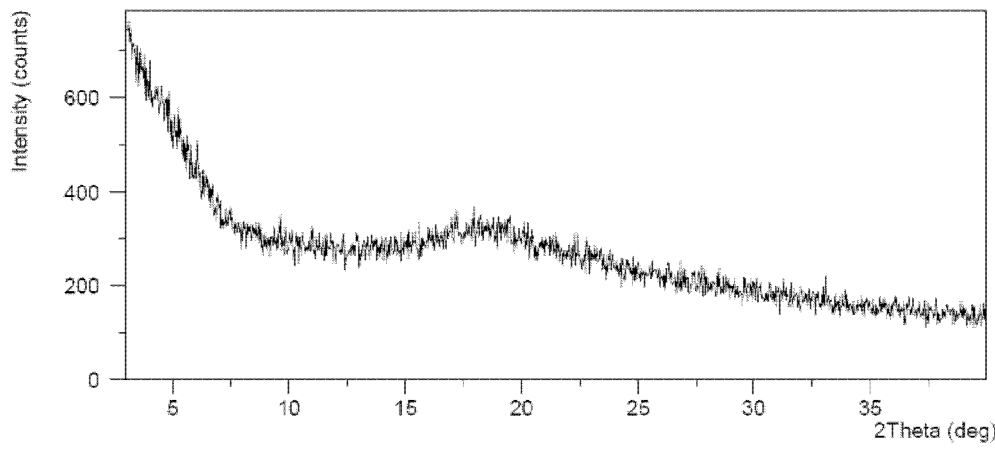
FIG. 10 is an XRPD pattern of Compound 1 monohydrochloride amorphous Form IV.
Figure 11:
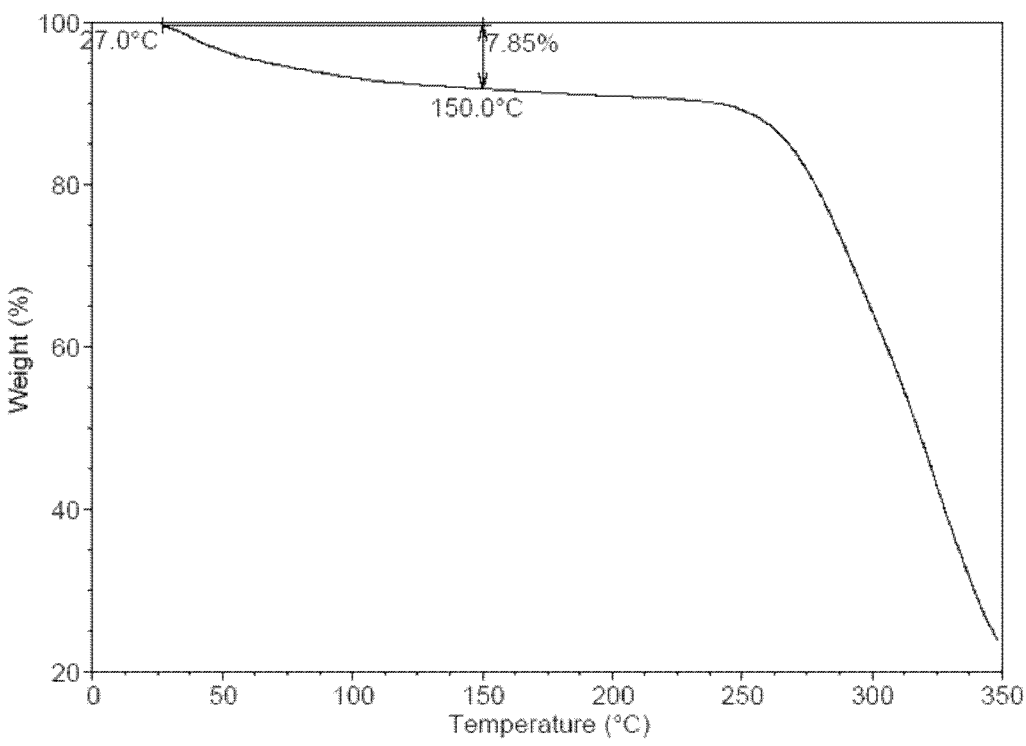
FIG. 11 is a TGA plot of Compound 1 monohydrochloride amorphous Form IV.
Figure 12:
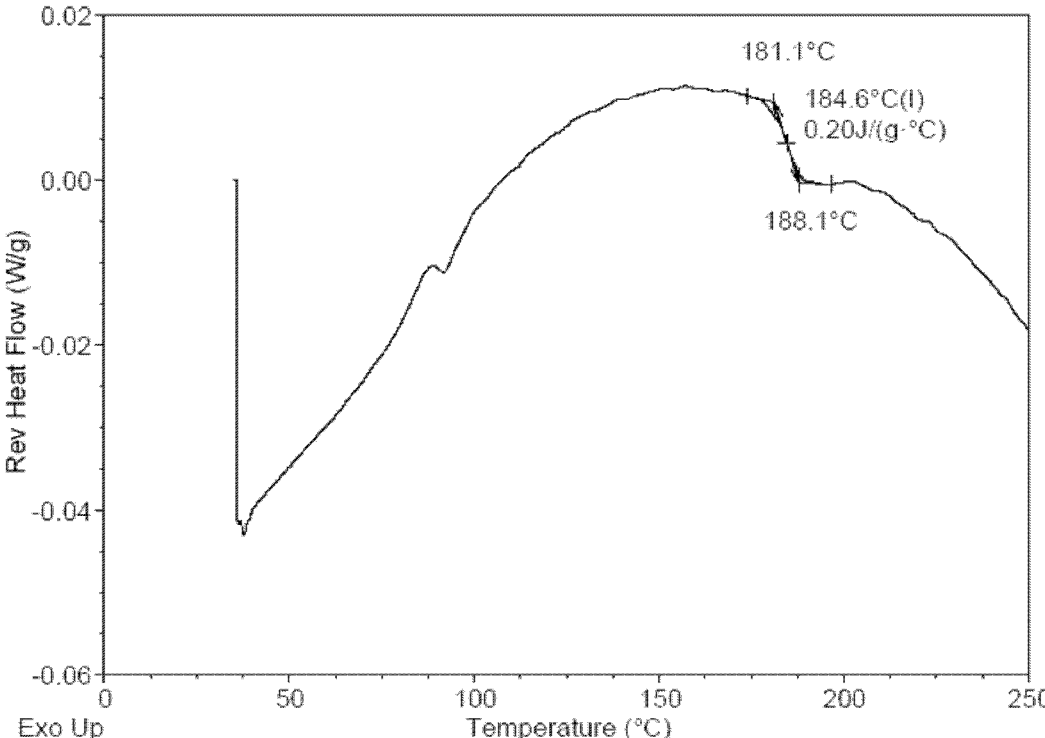
FIG. 12 is a mDSC curve of Compound 1 monohydrochloride amorphous Form IV.
Figure 16:
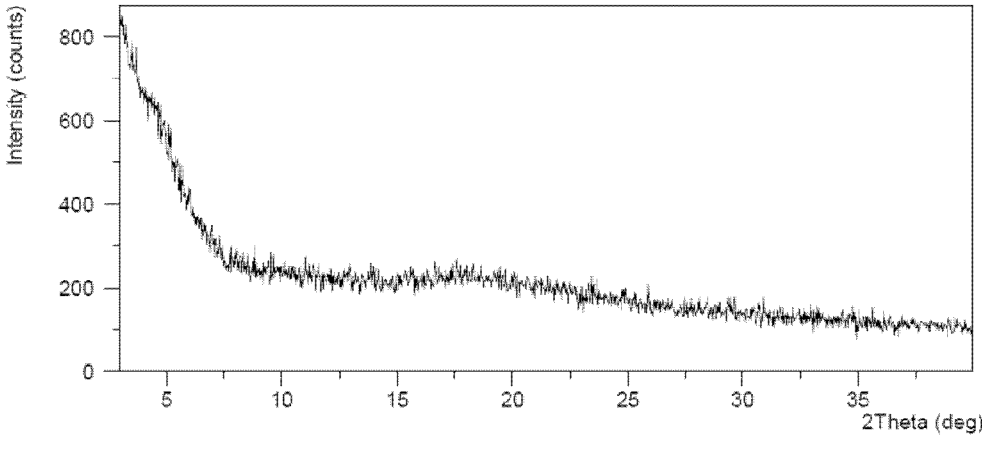
FIG. 16 is an XRPD pattern of Compound 1 sulfate amorphous form VI.
Figure 17:
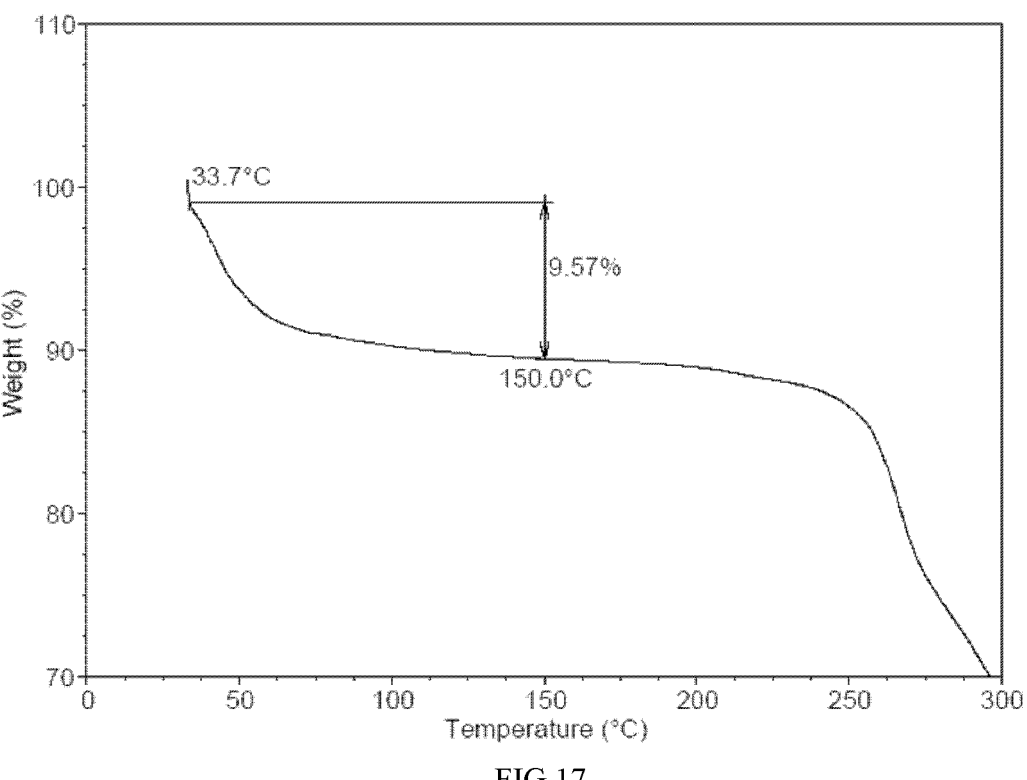
FIG. 17 is a TGA plot of Compound 1 sulfate amorphous form VI.
Figure 18:
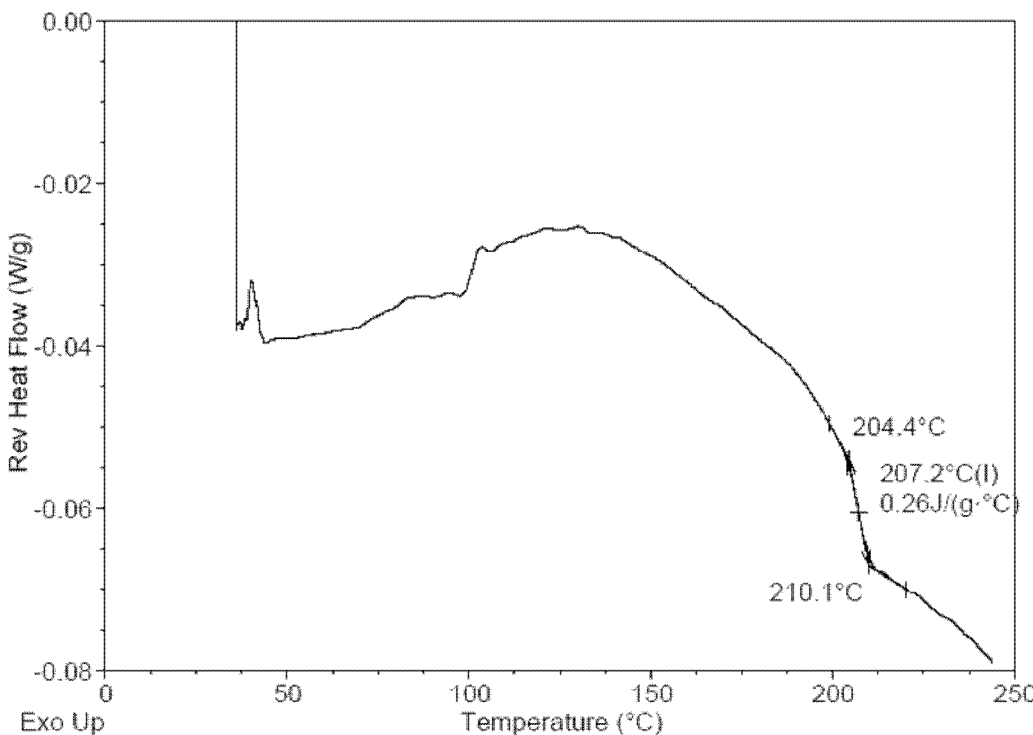
FIG. 18 is a mDSC curve of Compound 1 sulfate amorphous form VI.
Figures 19, 20:
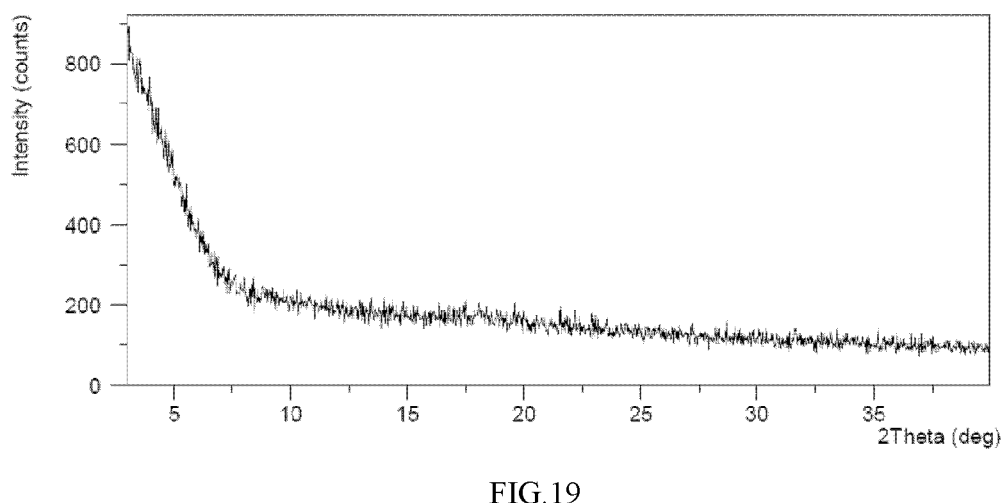
FIG. 19 is an XRPD pattern of Compound 1 phosphate amorphous Form VII.
FIG. 20 is a TGA plot of Compound 1 phosphate amorphous Form VII.
Figure 21:
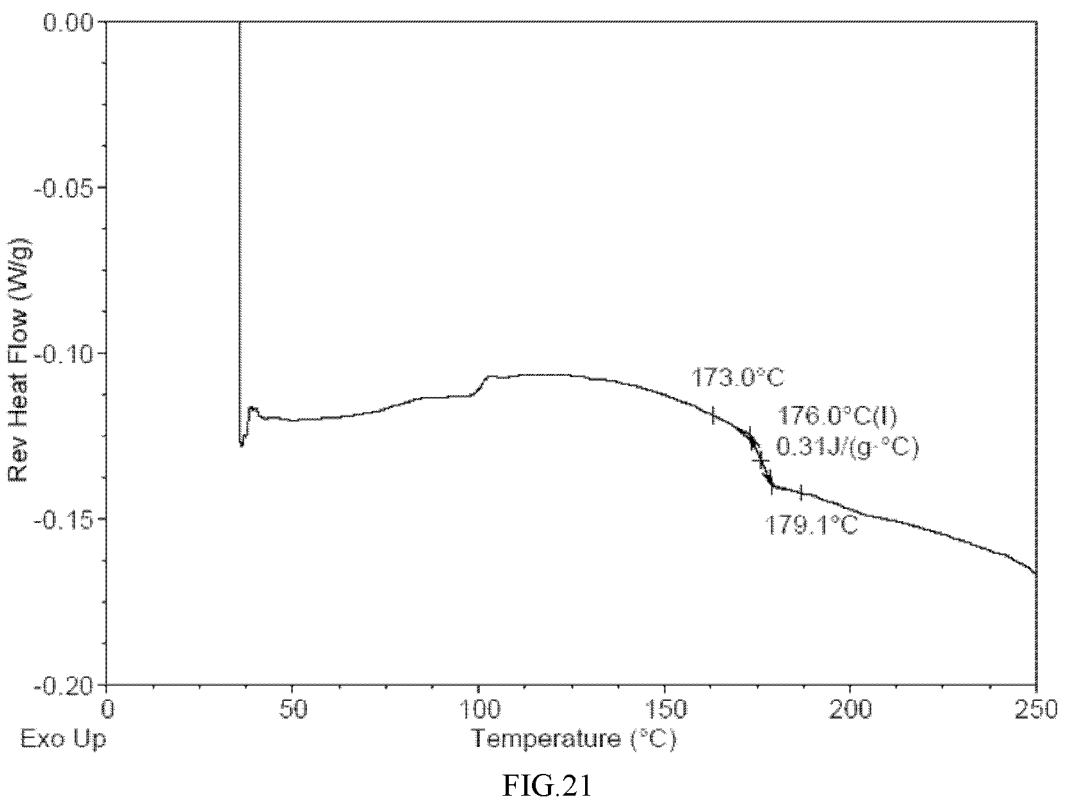
FIG. 21 is a mDSC curve of Compound 1 phosphate amorphous Form VII.
Figure 22:
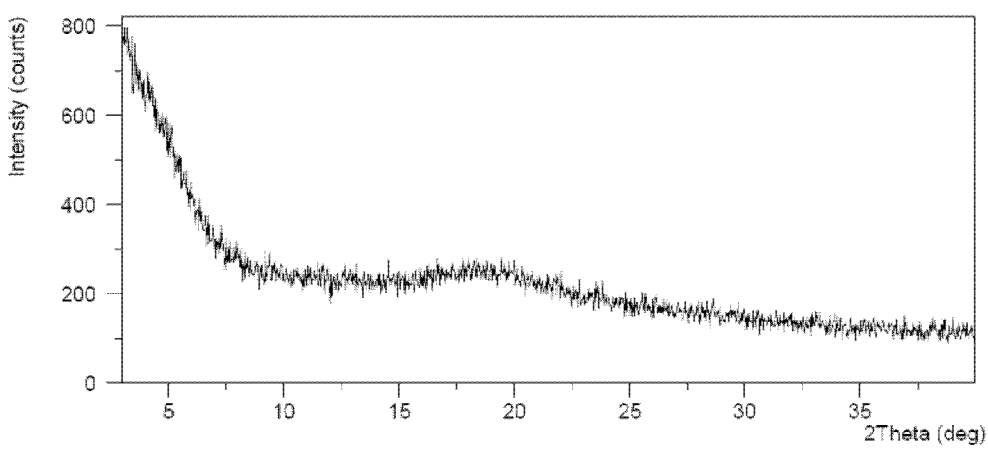
FIG. 22 is an XRPD pattern of Compound 1 mesylate amorphous form VIII.
Figures 23, 24:
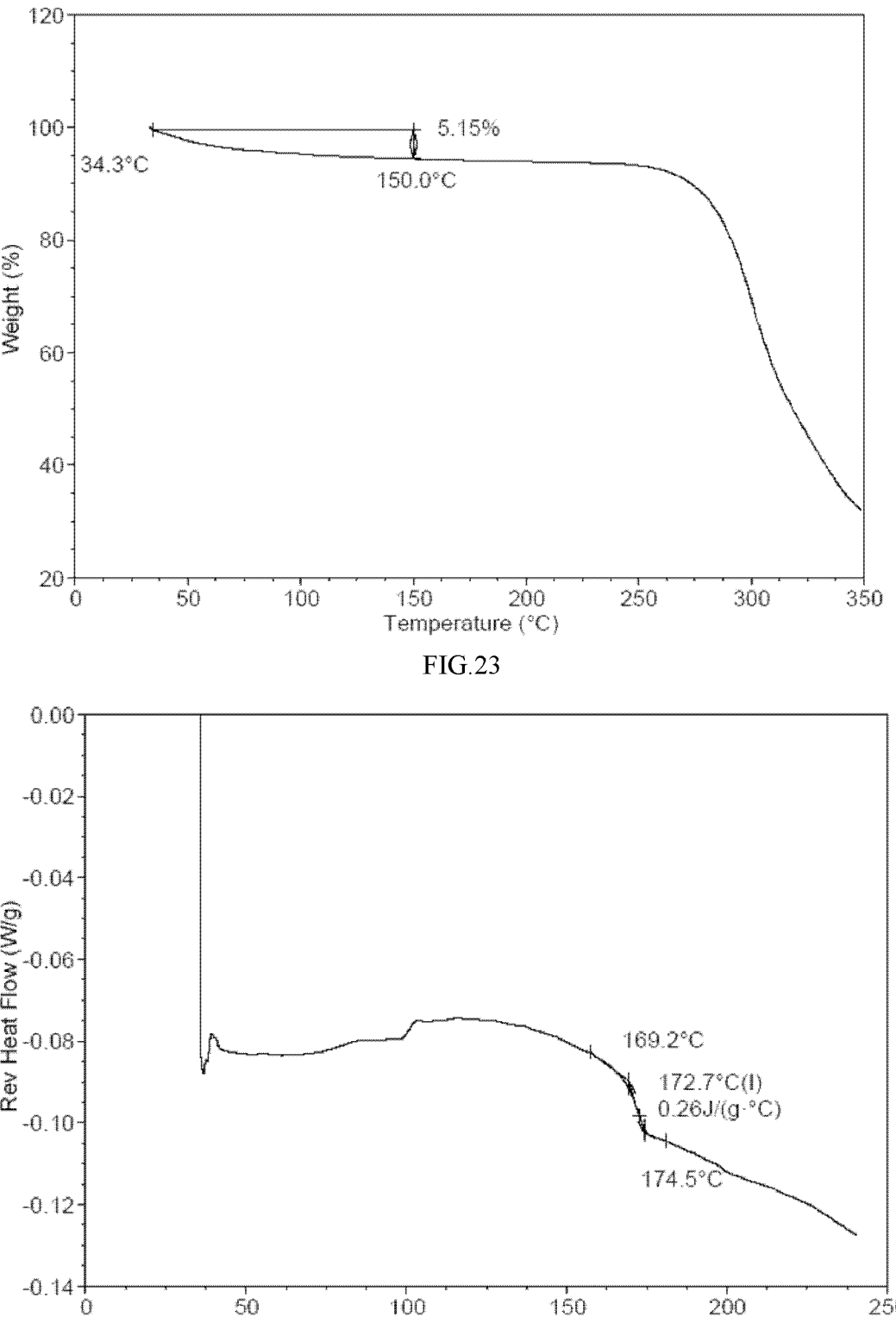
FIG. 23 is a TGA plot of Compound 1 mesylate amorphous form VIII.
FIG. 24 is a mDSC curve of Compound 1 mesylate amorphous form VIII.
Figure 25:
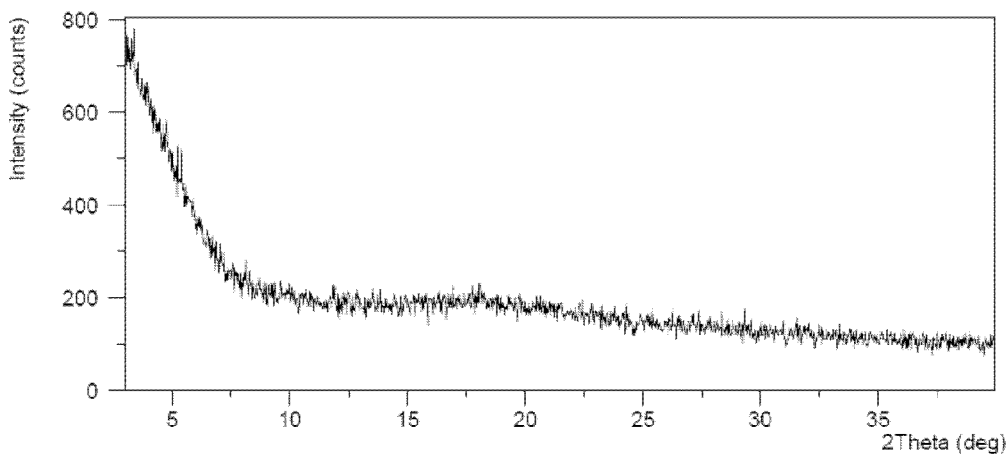
FIG. 25 is an XRPD pattern of Compound 1 maleate amorphous form IX.
Figure 26:
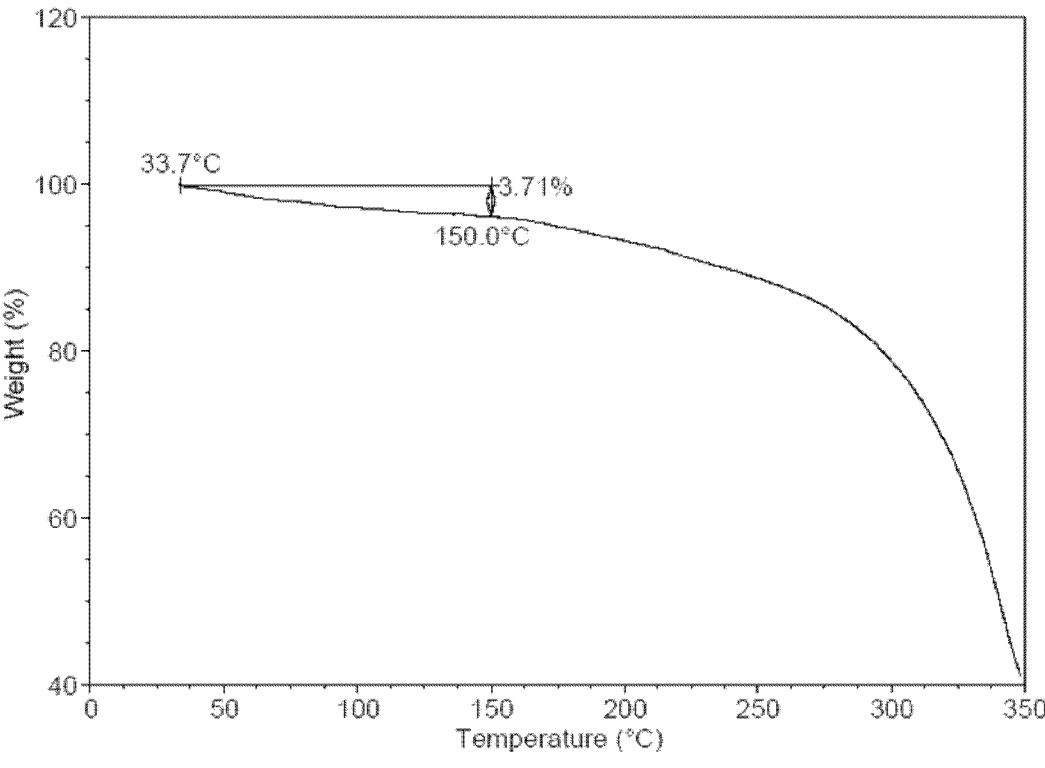
FIG. 26 is a TGA plot of Compound 1 maleate amorphous form IX.
Figure 27:
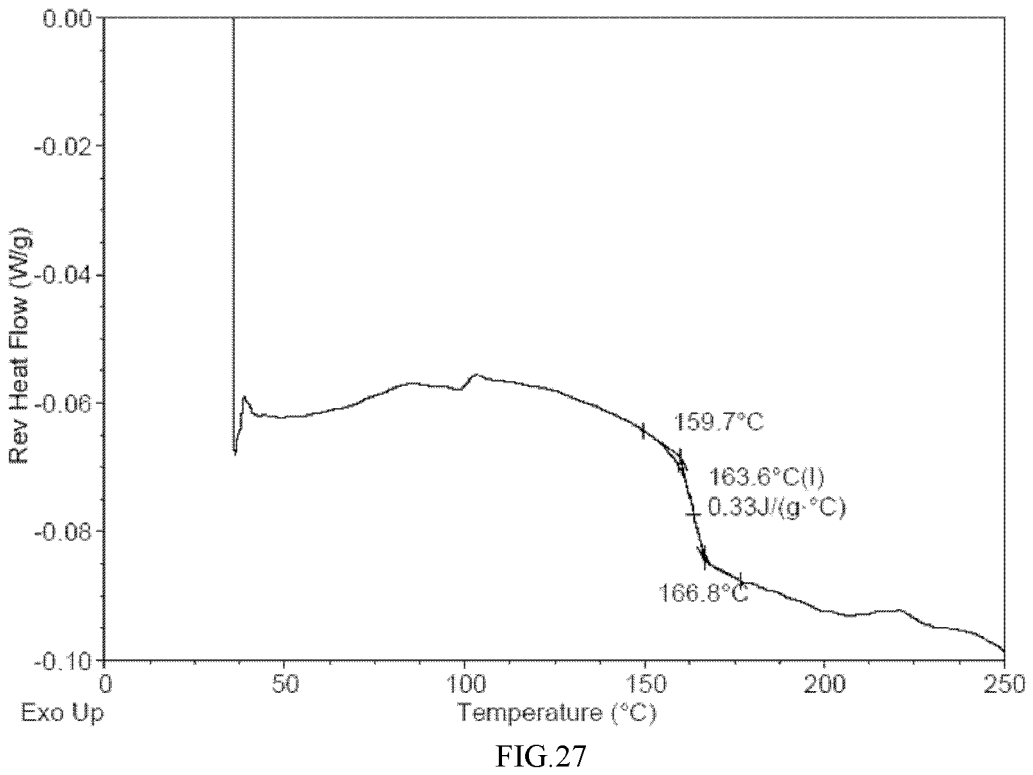
FIG. 27 is a mDSC curve of Compound 1 maleate amorphous form IX.
Figure 28:
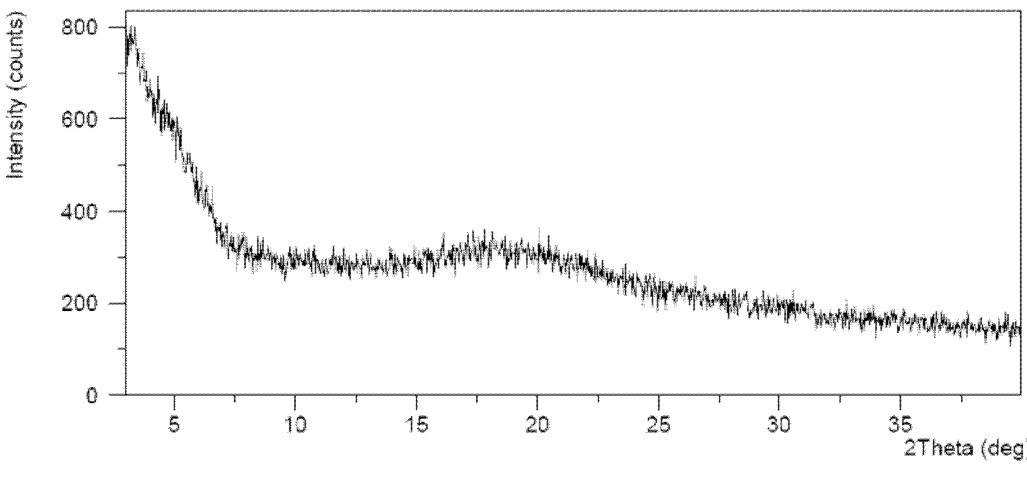
FIG. 28 is an XRPD pattern of Compound 1 tartrate amorphous form X.
Figure 29:
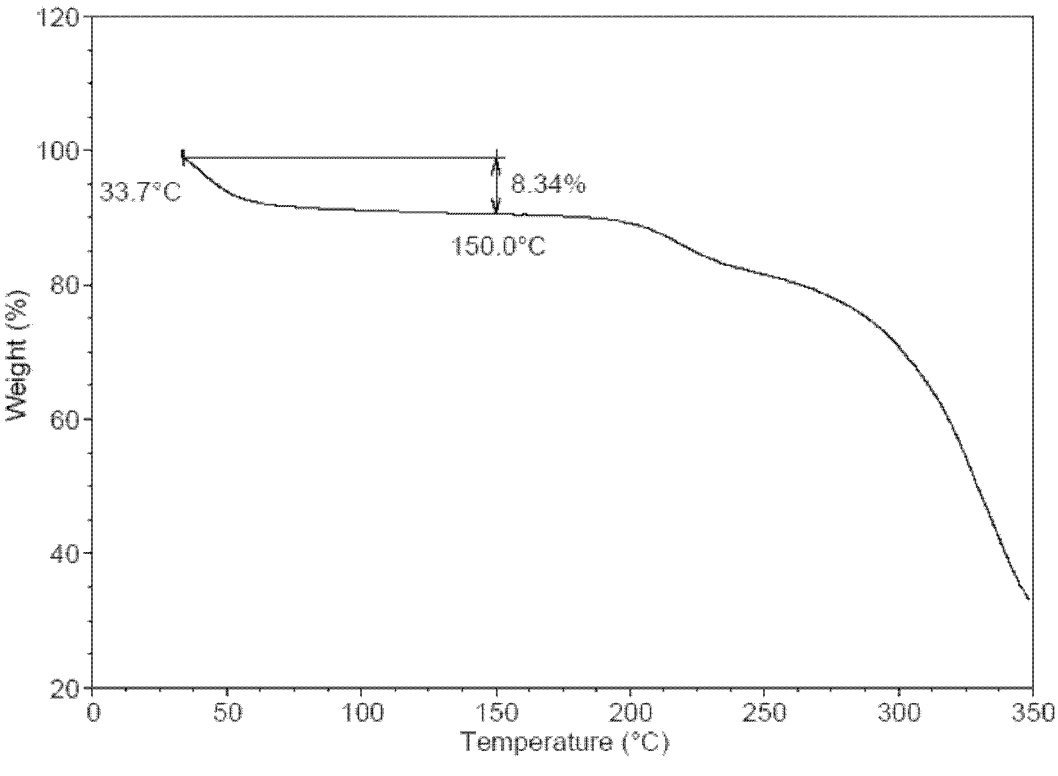
FIG. 29 is a TGA plot of Compound 1 tartrate amorphous form X.
Figure 30:
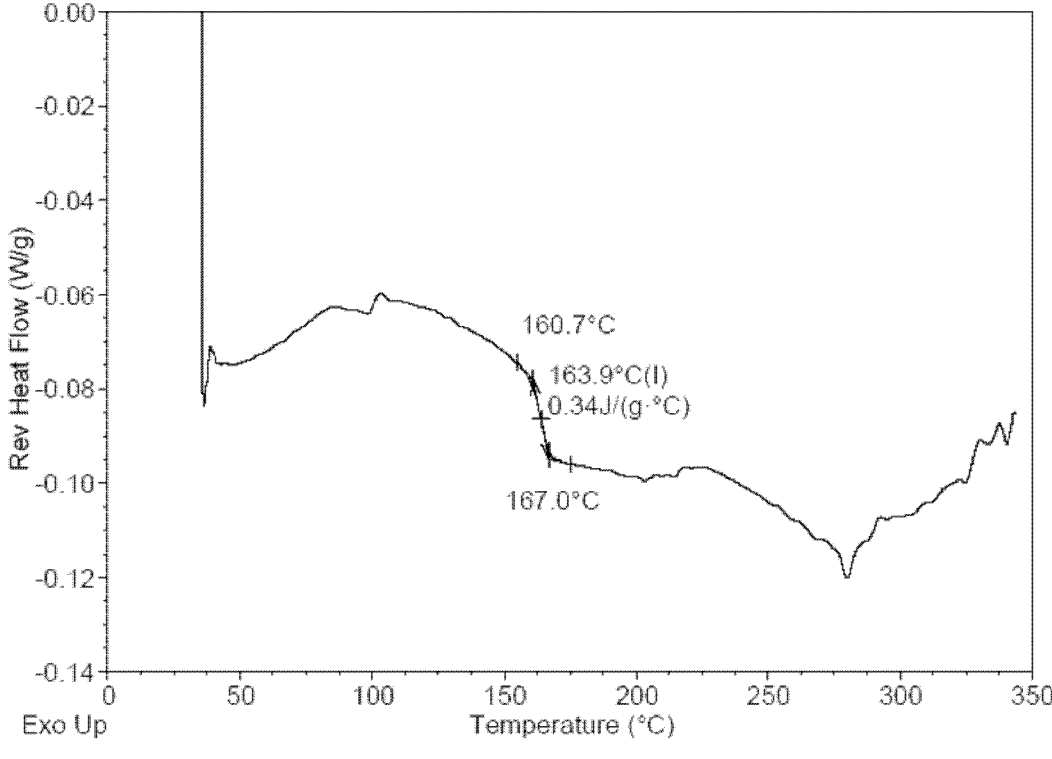
FIG. 30 is a mDSC curve of Compound 1 tartrate amorphous form X.
Figure 31:
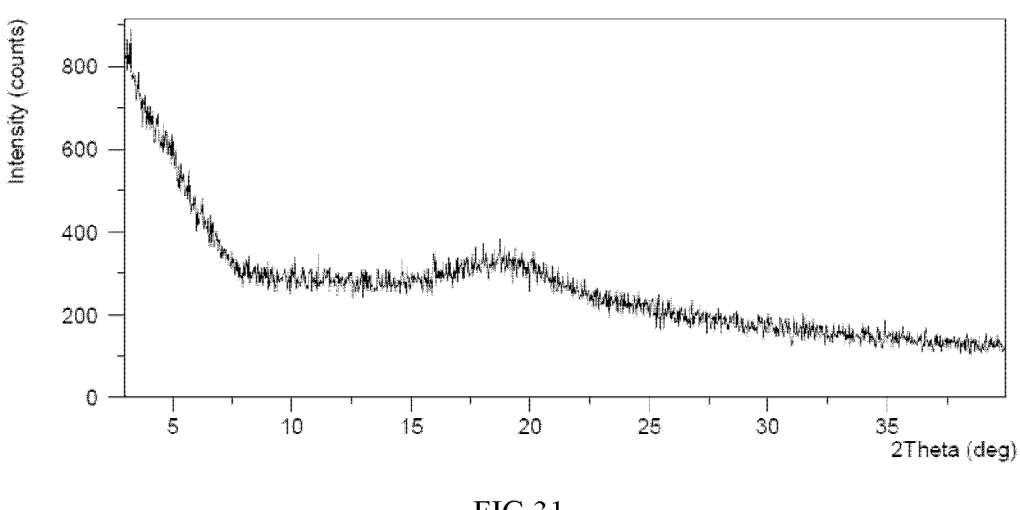
FIG. 31 is an XRPD pattern of Compound 1 benzoate amorphous Form XI.
Figure 32:
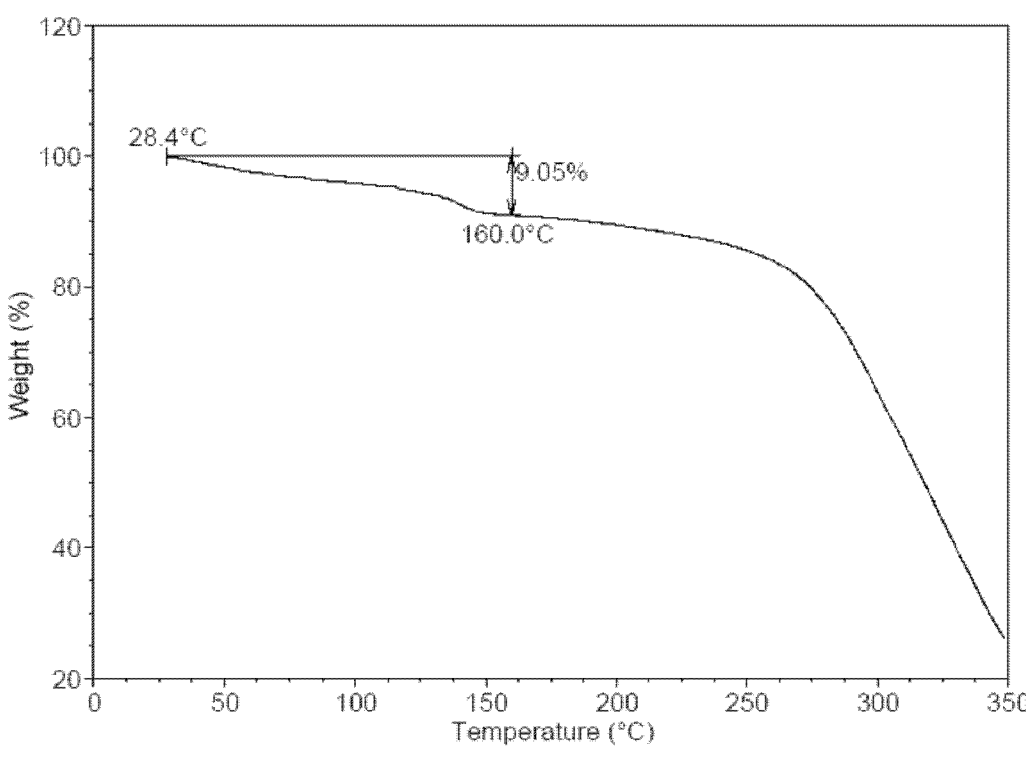
FIG. 32 is a TGA plot of Compound 1 benzoate amorphous Form XI.
Figure 33:
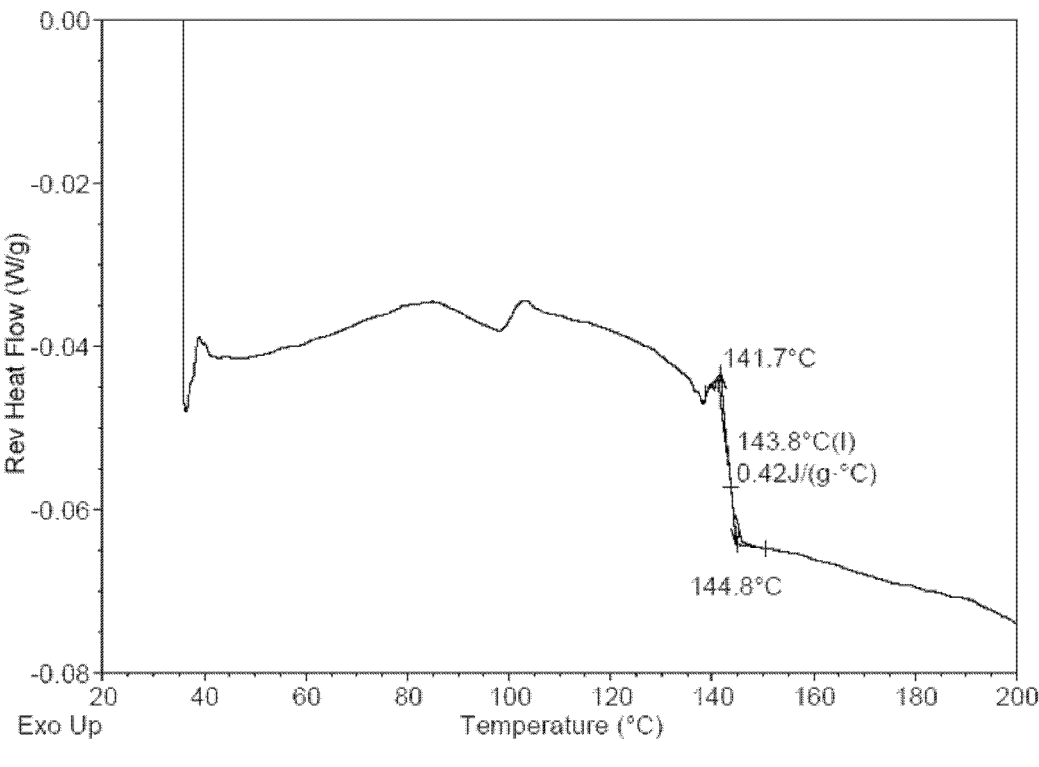
FIG. 33 is a mDSC curve of Compound 1 benzoate amorphous Form XI.
Figure 34:
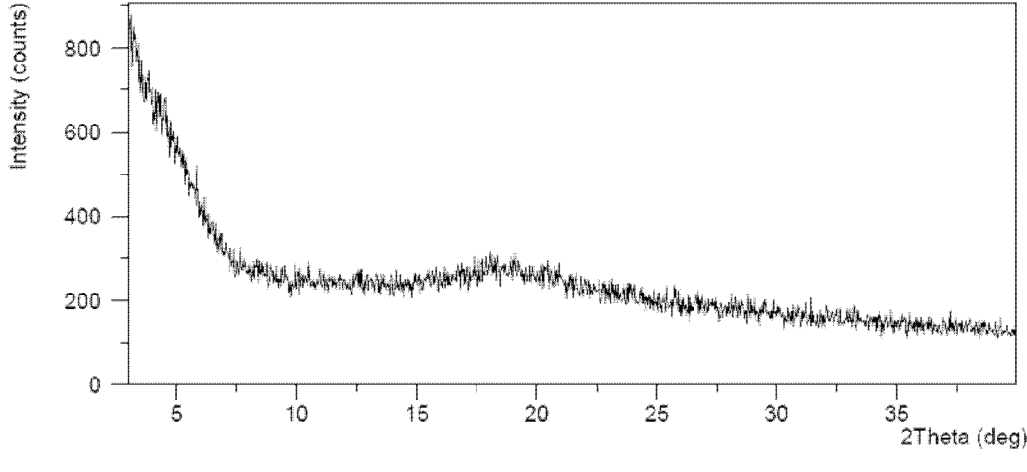
FIG. 34 is an XRPD pattern of Compound 1 succinate amorphous form XII.
Figure 35:
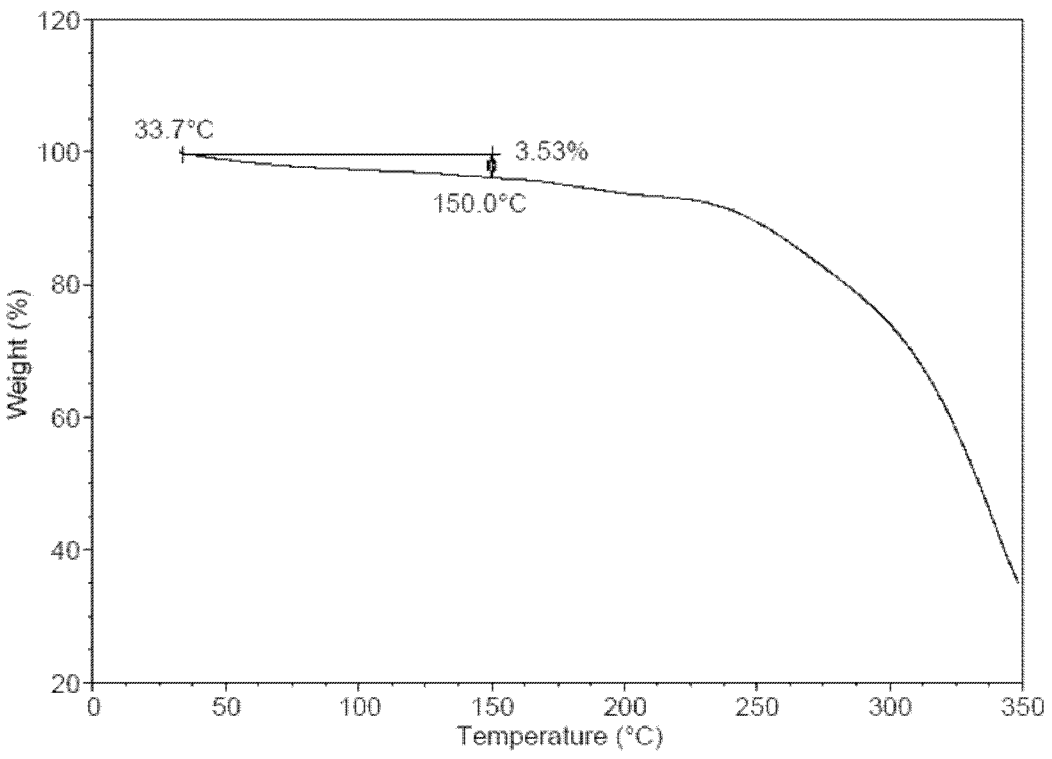
FIG. 35 is a TGA plot of Compound 1 succinate amorphous form XII.
Figure 36:
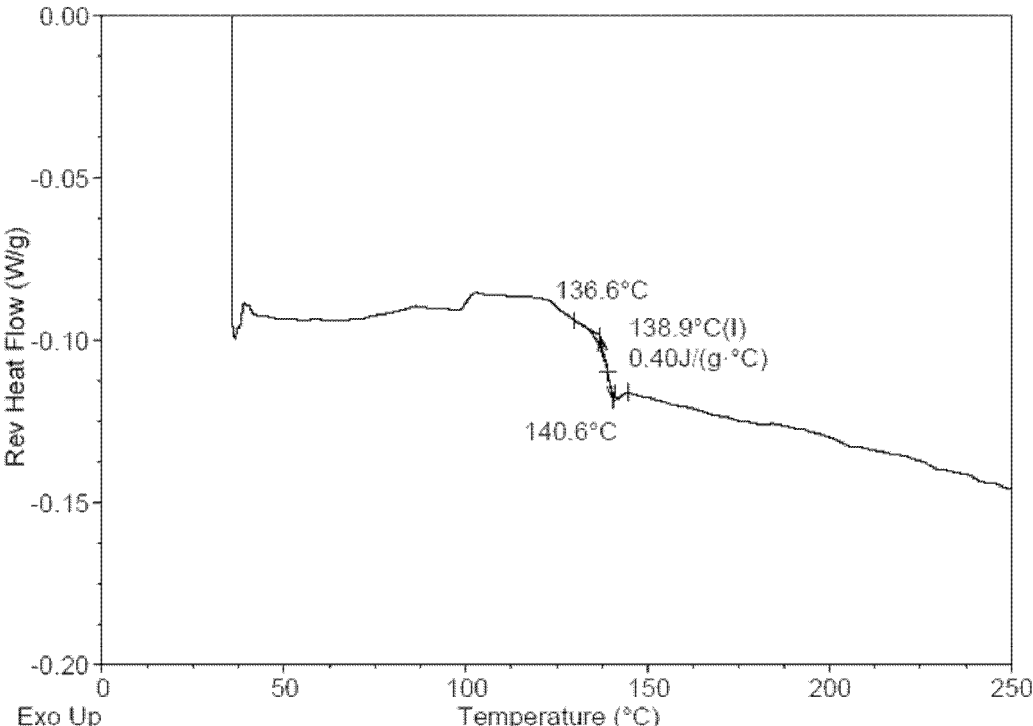
FIG. 36 is a mDSC curve of Compound 1 succinate amorphous form XII.
Figure 37:
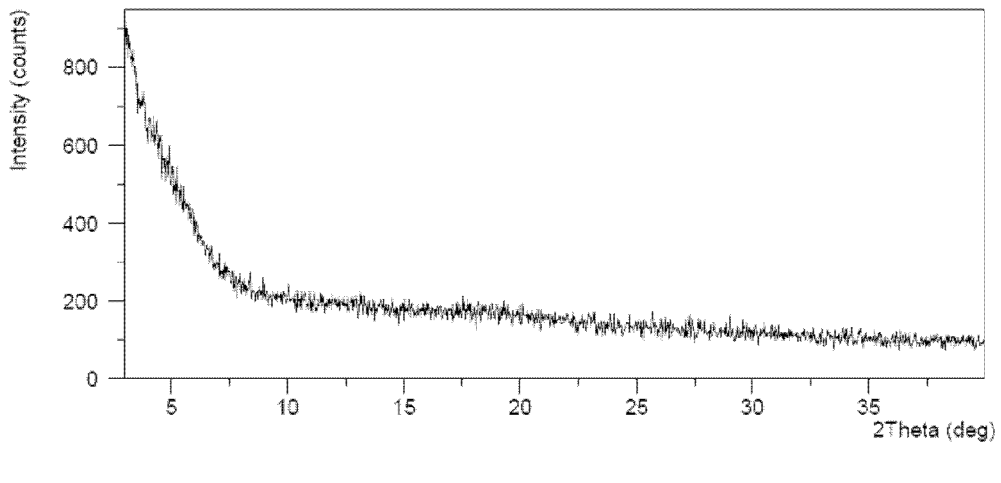
FIG. 37 is an XRPD pattern of Compound 1 acetate amorphous Form XIII.
Figure 38:
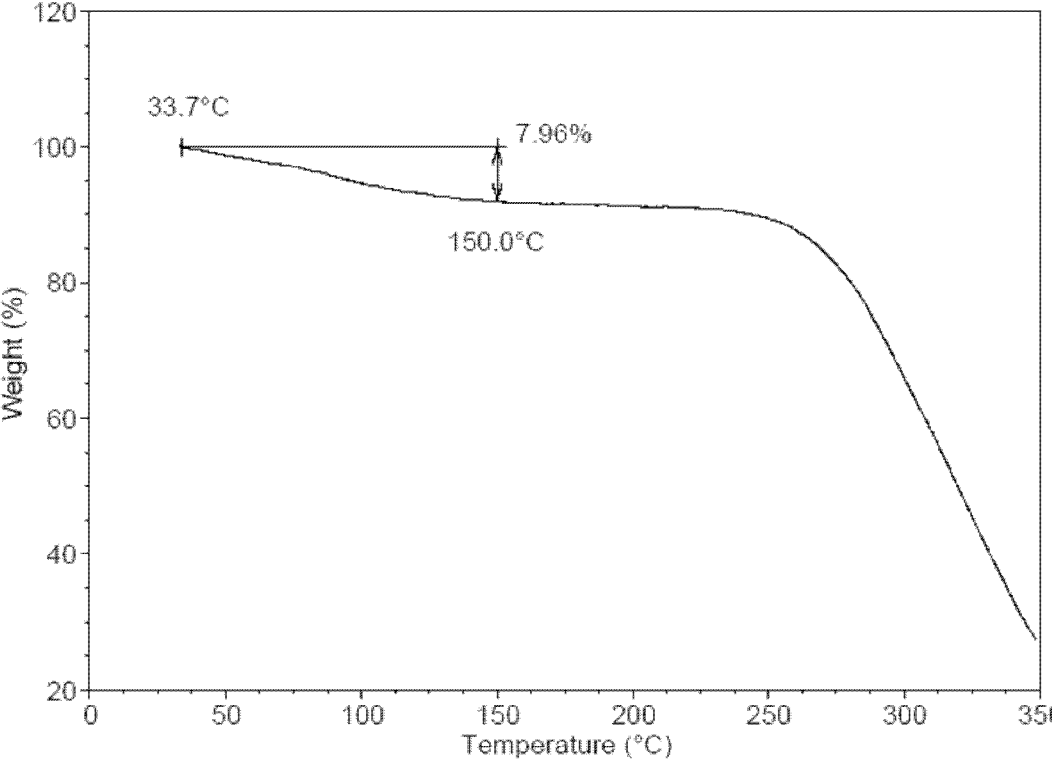
FIG. 38 is a TGA plot of Compound 1 acetate amorphous Form XIII.
Figure 39:
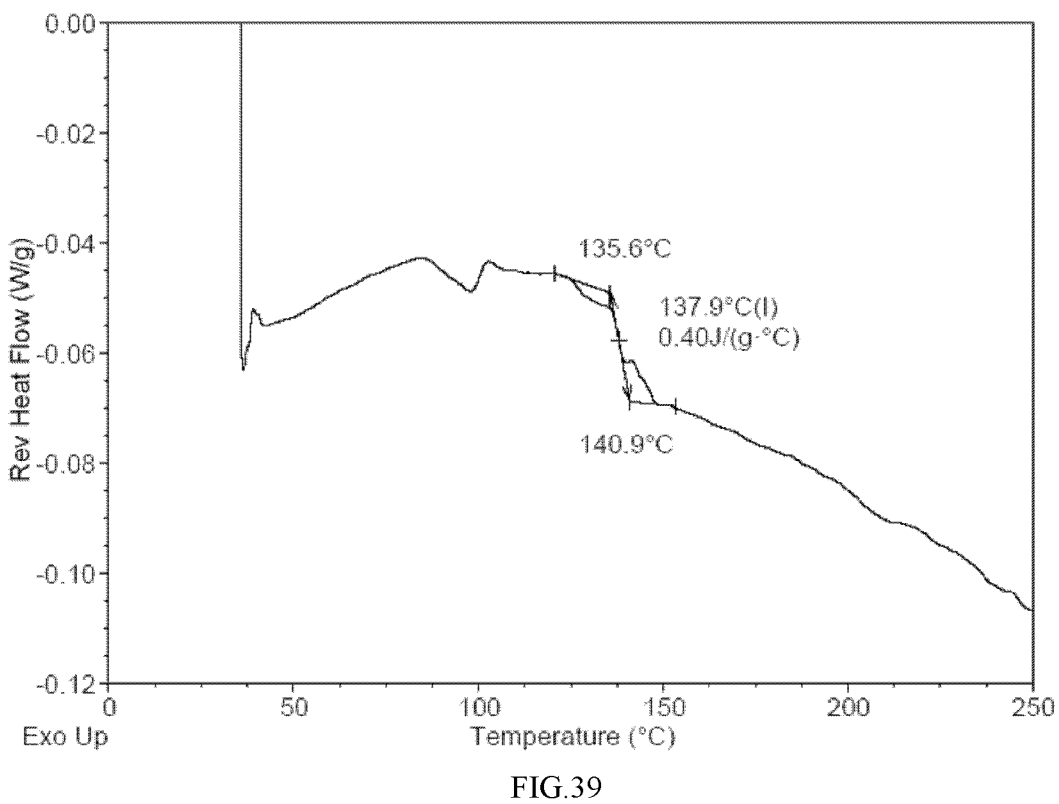
FIG. 39 is a mDSC curve of Compound 1 acetate amorphous Form XIII.
Figure 43:
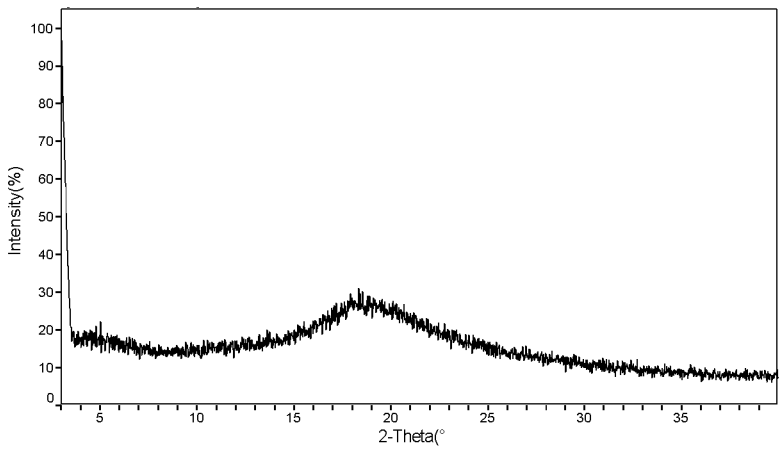
FIG. 43 is an XRPD pattern of Compound 1 P-toluenesulfonate amorphous Form XV.
Figure 44:
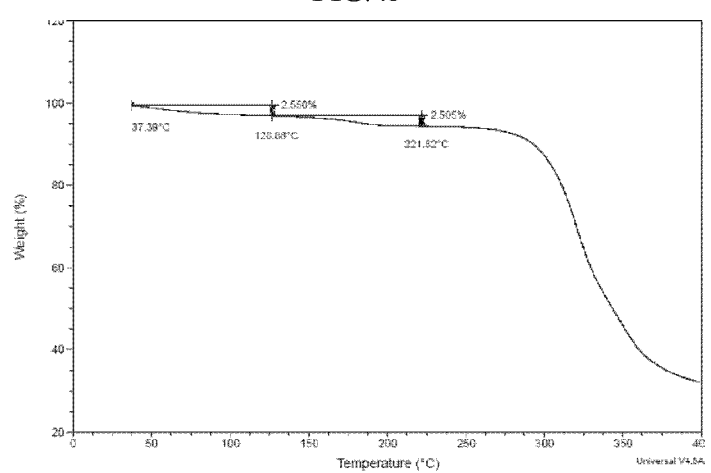
FIG. 44 is a TGA plot of Compound 1 P-toluenesulfonate amorphous Form XV
Figure 45:
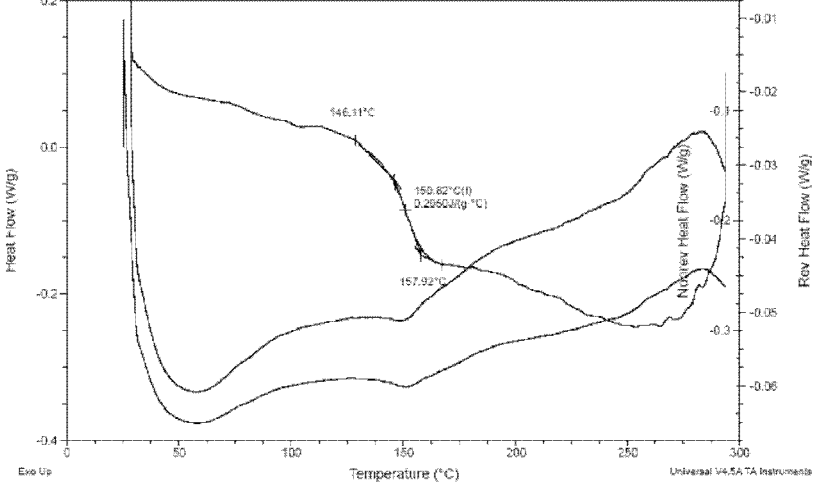
FIG. 45 is a mDSC curve of Compound 1 P-toluenesulfonate amorphous Form XV.
Figure 46:
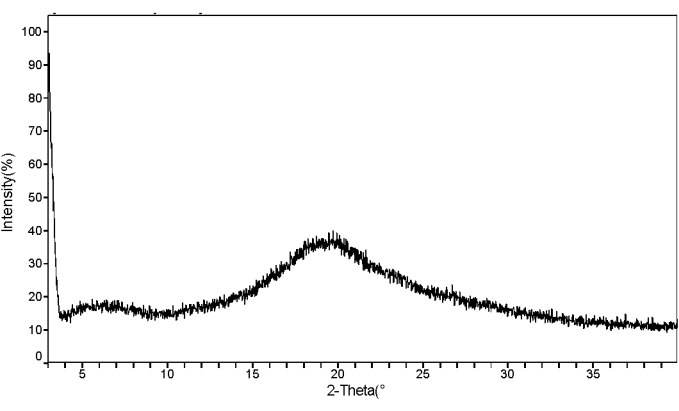
FIG. 46 is an XRPD pattern of Compound 1 di-p-toluenesulfonate amorphous Form XVI.
Figure 47:
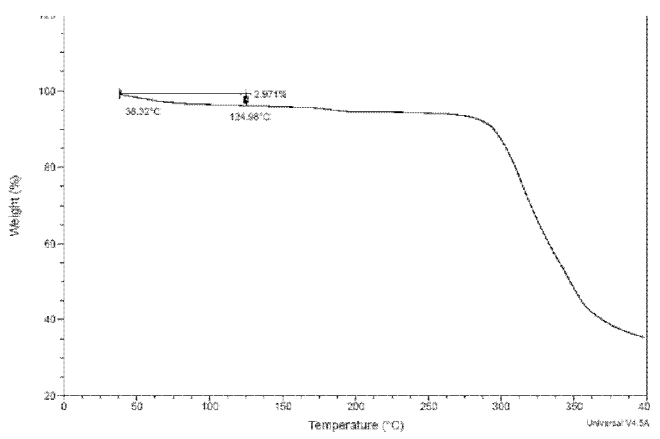
FIG. 47 is a TGA plot of Compound 1 di-p-toluenesulfonate amorphous Form XVI
Figure 48:
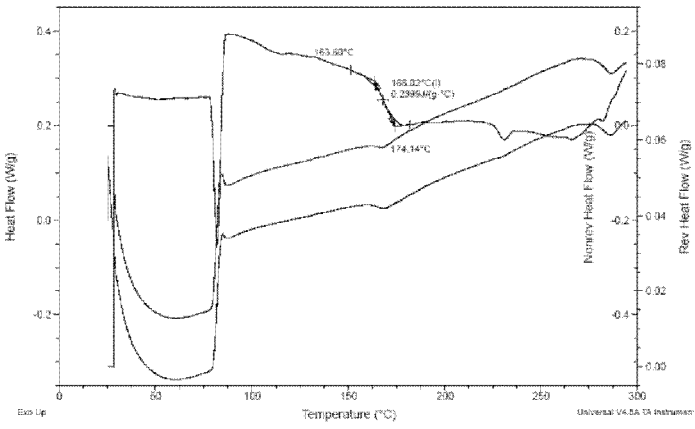
FIG. 48 is a mDSC curve of Compound 1 di-p-toluenesulfonate amorphous Form XVI.
Figure 49:
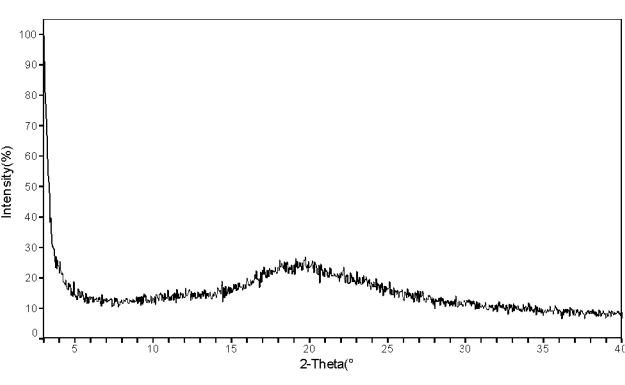
FIG. 49 is an XRPD pattern of Compound 1 diphosphate amorphous Form XVII.
Figure 50:
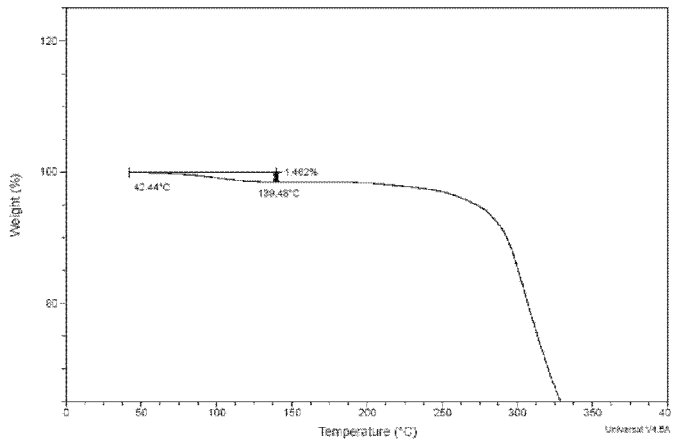
FIG. 50 is a TGA plot of Compound 1 diphosphate amorphous Form XVII.
Figure 51:
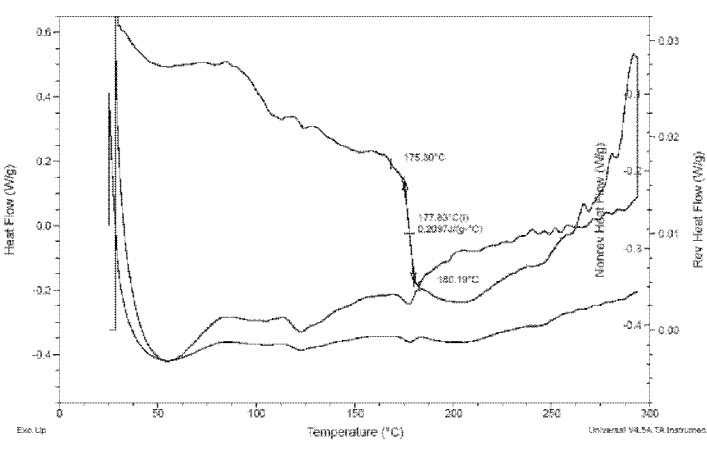
FIG. 51 is a mDSC curve of Compound 1 diphosphate amorphous Form XVII.
Figure 52:
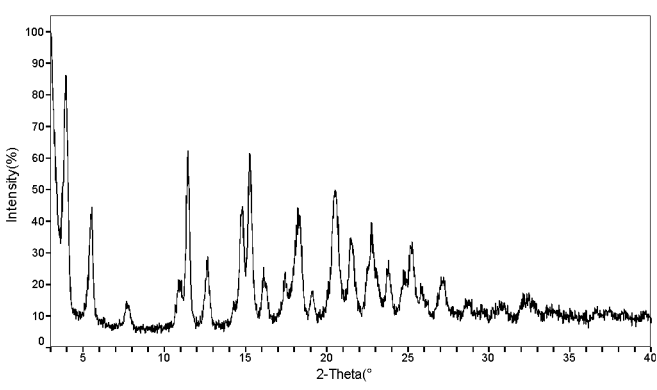
FIG. 52 is an XRPD pattern of Compound 1 dimethanesulfonate crystalline Form XVIII.
Figure 53:
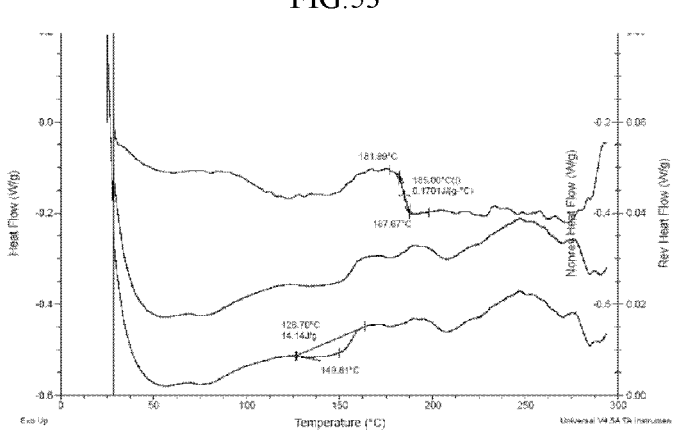
FIG. 53 is a TGA plot of Compound 1 dimethanesulfonate crystalline Form XVIII.
Figure 54:
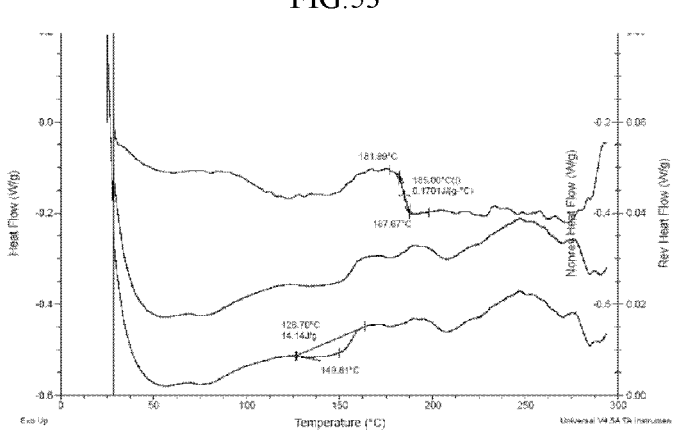
FIG. 54 is a mDSC curve of Compound 1 dimethanesulfonate crystalline Form XVIII.
Figure 55:
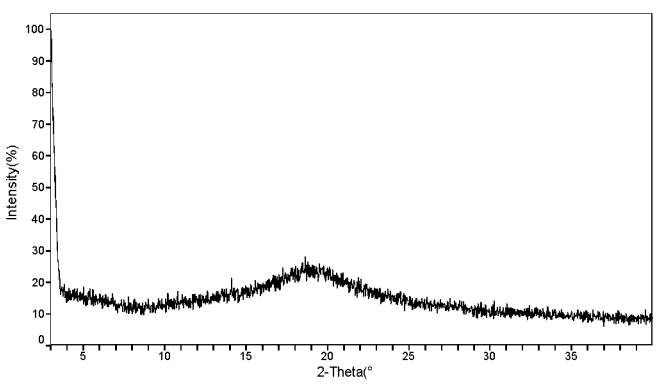
FIG. 55 is an XRPD pattern of Compound 1 oxalate amorphous Form XIX.
Figure 56:
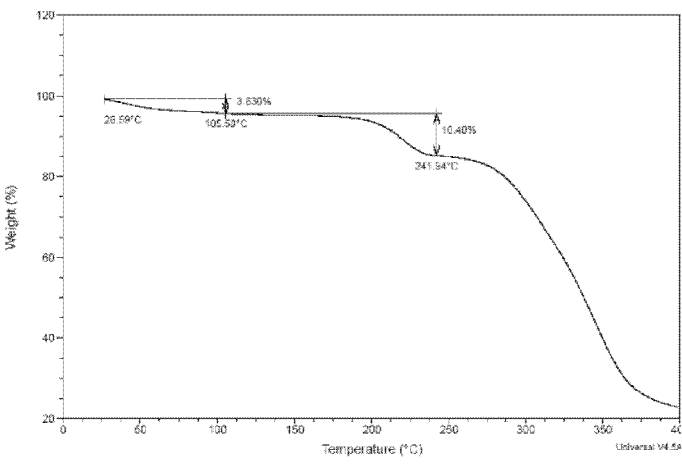
FIG. 56 is a TGA plot of Compound 1 oxalate amorphous Form XIX.
Figure 57:
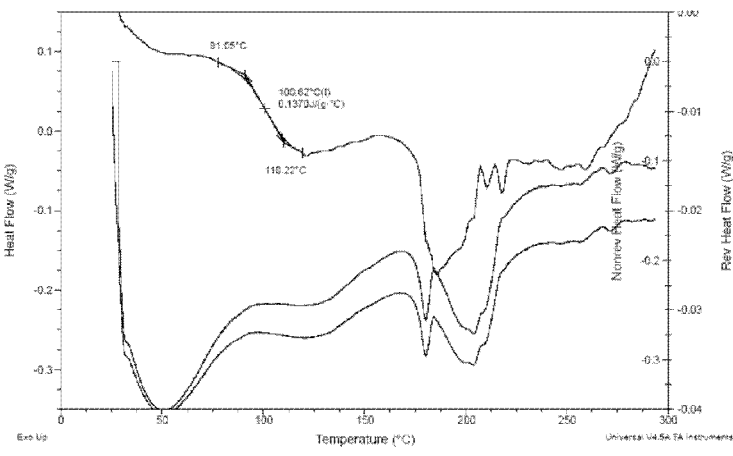
FIG. 57 is a mDSC curve of Compound 1 oxalate amorphous Form XIX.
Figure 58:
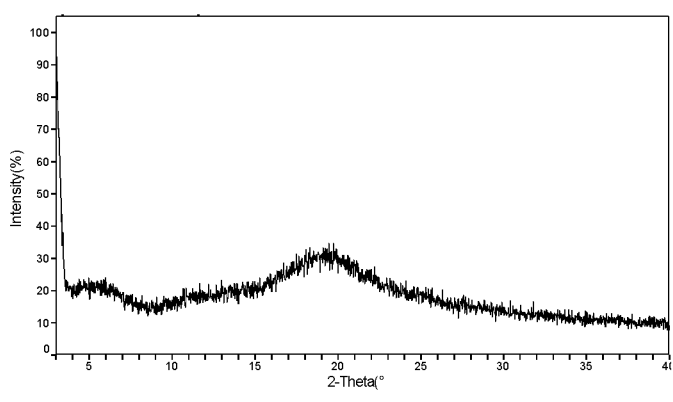
FIG. 58 is an XRPD pattern of Compound 1 dioxalate amorphous Form XX.
Figure 59:
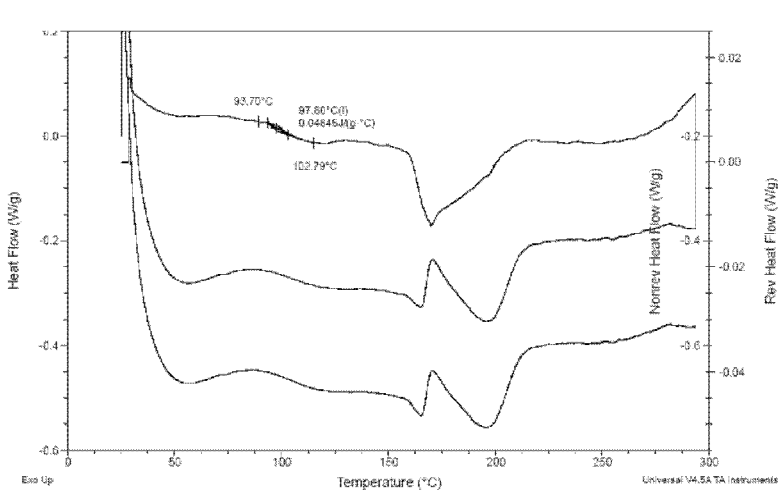
FIG. 59 is a TGA plot of Compound 1 dioxalate amorphous Form XX.
Figure 60:
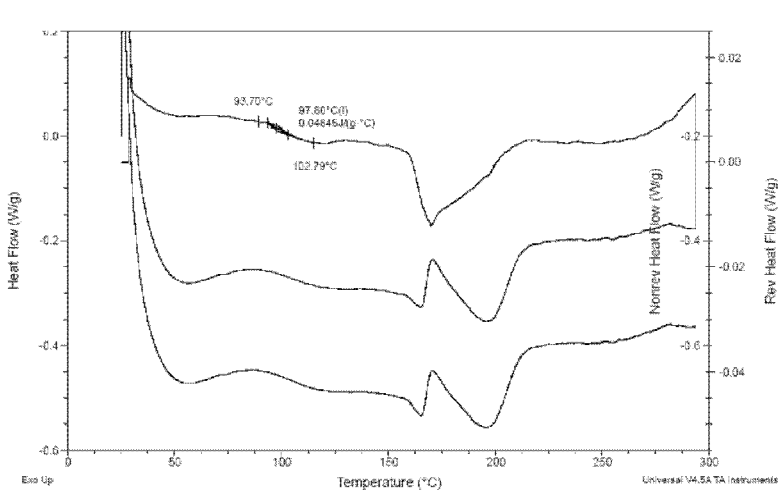
FIG. 60 is a mDSC curve of Compound 1 dioxalate amorphous Form XX.
Figure 61:
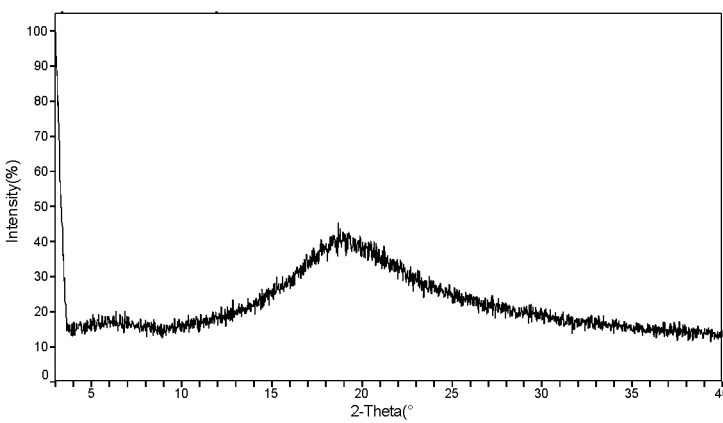
FIG. 61 is an XRPD pattern of Compound 1 dimaleate amorphous Form XXI.
Figure 62:
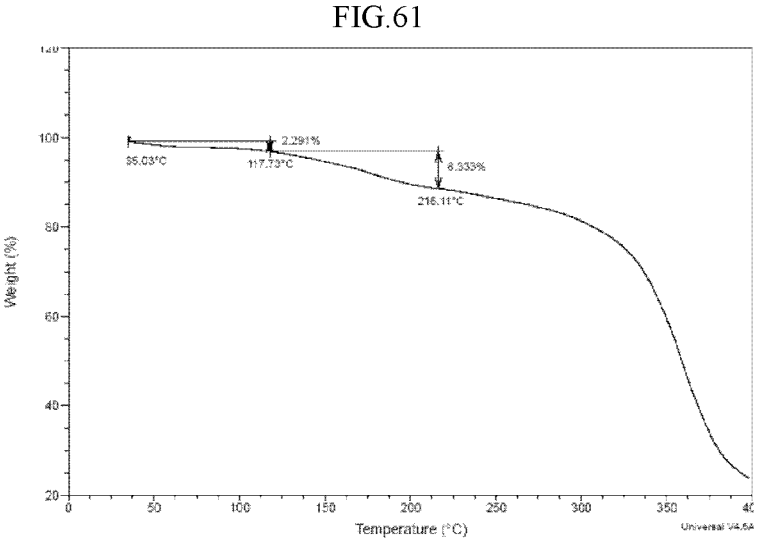
FIG. 62 is a TGA plot of Compound 1 dimaleate amorphous Form XXI.
Figure 63:
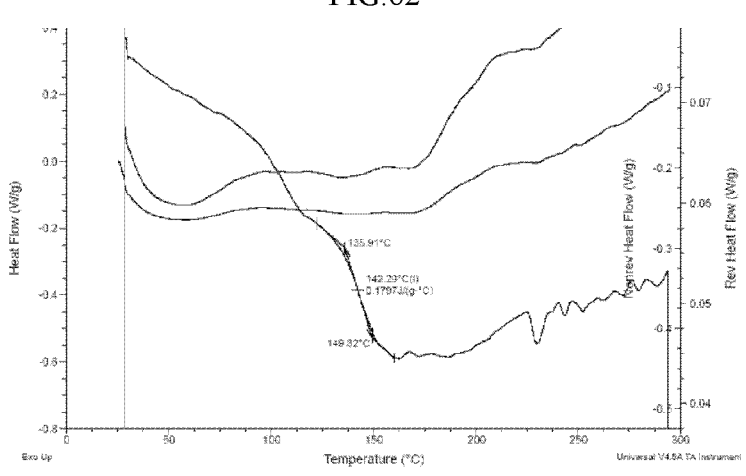
FIG. 63 is a mDSC curve of Compound 1 dimaleate amorphous Form XXI.
Figure 67:
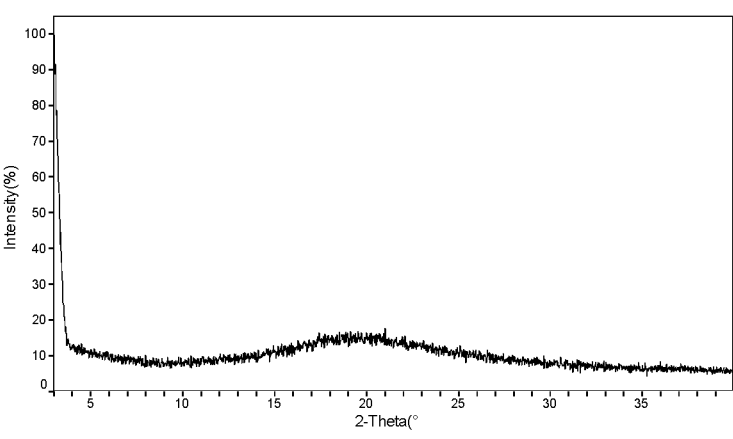
FIG. 67 is an XRPD pattern of Compound 1 disulfate amorphous Form XXIII.
Figure 68:
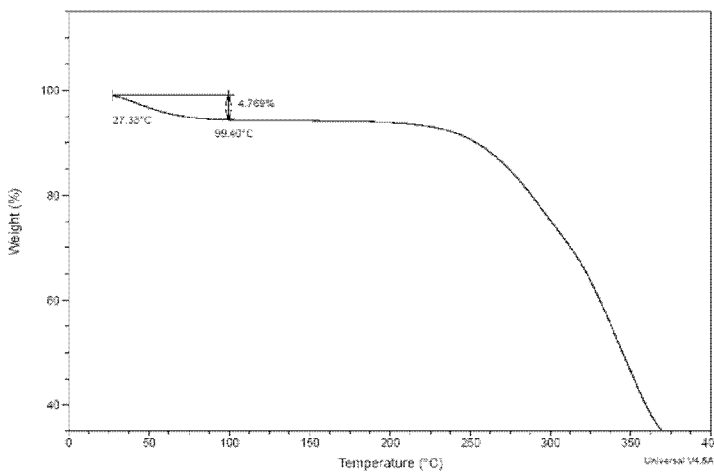
FIG. 68 is a TGA plot of Compound 1 disulfate amorphous Form XXIII.

7. A crystalline or amorphous form of a salt of compound 1:

(compound 1)

wherein the crystalline or amorphous form of the salt of compound 1 is amorphous form IV of compound 1 monohydrochloride, characterized by an X-ray powder diffraction pattern as shown in FIG. 10, and optionally has the following characteristics:

1) In a TGA plot, there is a weight loss of 7.9±0.2% by weight before 150° C.;

2) In a mDSC curve, there is a glassy transition temperature at the midpoint temperature of 184.6±2.0° C.;

3a TGA plot as shown in FIG. 11; and/or 4) a mDSC curve as shown in FIG. 12;

or amorphous form VI of compound 1 sulfate, characterized by an X-ray powder diffraction pattern as shown in FIG. 16, and optionally has the following characteristics:

1) In a TGA plot, there is a weight loss of 9.6±0.2% by weight before 150° C.;

2 In a mDSC curve, there is a glassy transition temperature at the midpoint temperature of 207.2+2.0° C.;

3) a TGA plot as shown in FIG. 17; and/or 4) a mDSC curve as shown in FIG. 18;

or amorphous form VII of compound 1 phosphate, characterized by an X-ray powder diffraction pattern as shown in FIG. 19, and optionally has the following characteristics:

1) a TGA plot, there is a weight loss of 4.5±0.2% by weight before 150° C.;

2) In a mDSC curve, there is a glassy transition temperature at the midpoint temperature of 176.0±2.0° C.;

3) a TGA plot as shown in FIG. 20; and/or 4) a mDSC curve as shown in FIG. 21;

or amorphous form VIII of compound 1 mesylate, characterized by an X-ray powder diffraction pattern as shown in FIG. 22, and optionally has the following characteristics:

1) In a TGA plot, there is a weight loss of 5.2±0.2% by weight before 150° C.;

2) In a mDSC curve, there is a glassy transition temperature at the midpoint temperature of 172.7±2.0° C.;

3) a TGA plot as shown in FIG. 23; and/or 4) a mDSC curve as shown in FIG. 24;

or amorphous form IX of compound 1 maleate, characterized by an X-ray powder diffraction pattern as shown in FIG. 25, and optionally has the following characteristics:

1) In a TGA plot, there is a weight loss of 3.7±0.2% by weight before 150° C.;

2) In a mDSC curve, there is a glassy transition temperature at the midpoint temperature of 163.6±2.0° C.;

3) a TGA plot as shown in FIG. 26; and/or 4) a mDSC curve substantially as shown in FIG. 27;

or amorphous form X of compound 1 tartrate, characterized by an X-ray powder diffraction pattern as shown in FIG. 28, and optionally has the following characteristics:

1) In a TGA plot, there is a weight loss of 8.3±0.2% by weight before 150° C.;

2) In a mDSC curve, there is a glassy transition temperature at the midpoint temperature of 163.9±2.0° C.;

3) a TGA plot as shown in FIG. 29; and/or 4) a mDSC curve as shown in FIG. 30;

or amorphous form XI of compound 1 benzoate, characterized by an X-ray powder diffraction pattern as shown in FIG. 31, and optionally has the following characteristics:

1) In a TGA plot, there is a weight loss of 9.1±0.2% by weight before 150° C.;

2) In a mDSC curve, there is a glassy transition temperature at the midpoint temperature of 143.8±2.0° C.;

3) a TGA plot as shown in FIG. 32; and/or 4) a mDSC curve as shown in FIG. 33;

or amorphous form XII of compound 1 succinate, characterized by an X-ray powder diffraction pattern as shown in FIG. 34, and optionally has the following characteristics:

1) In a TGA plot, there is a weight loss of 3.5±0.2% by weight before 150° C.;

2) In a mDSC curve, there is a glassy transition temperature at the midpoint temperature of 138.9±2.0° C.;

3) a TGA plot as shown in FIG. 35; and/or 4) a mDSC curve as shown in FIG. 36;

or amorphous form XIII of compound 1 acetate, characterized by an X-ray powder diffraction pattern as shown in FIG. 37, and optionally has the following characteristics:

1) In a TGA plot, there is a weight loss of 8.0±0.2% by weight before 150° C.;

2) In a mDSC curve, there is a glassy transition temperature at the midpoint temperature of 137.9±2.0° C.;

3) a TGA plot as shown in FIG. 38; and/or 4) a mDSC curve as shown in FIG. 39;

or amorphous form XV of compound 1 mono-p-toluenesulfonate, characterized by an X-ray powder diffraction pattern as shown in FIG. 43, and optionally has the following characteristics:

1) In a TGA plot, there is a weight loss of 2.55±0.2% by weight before 127° C.; and a weight loss of 2.51±0.2% by weight between 127° C. and 222° C.;

2) In a mDSC curve, there is a glassy transition temperature at the midpoint temperature of 150.82±2.0° C.;

3) a TGA plot as shown in FIG. 44; and/or 4) a mDSC curve as shown in FIG. 45;

or the amorphous form XVI of compound 1 di-p-toluenesulfonate, characterized by an X-ray powder diffraction pattern as shown in FIG. 46, and optionally has the following characteristics:

1) In a TGA plot, there is a weight loss of 2.97±0.2% by weight before 125° C.;

2) In a mDSC curve, there is a glassy transition temperature at the midpoint temperature of 168.02±2.0° C.;

3) a TGA plot as shown in FIG. 47; and/or 4) a mDSC curve as shown in FIG. 48;

or amorphous form XVII of compound 1 diphosphate characterized by an X-ray powder diffraction pattern as shown in FIG. 49, and optionally has the following characteristics:

1) In a TGA plot, there is a weight loss of 1.46±0.2% by weight before 140° C.;

2) In a mDSC curve, there is a glassy transition temperature at the midpoint temperature of 177.83±2.0° C.;

3) a TGA plot as shown in FIG. 50; and/or 4) a mDSC curve as shown in FIG. 51;

or crystalline form XVIII of compound 1 dimethanesulfonate, characterized by an X-ray powder diffraction pattern which has at least one or two peaks at 3.94±0.2°, 5.53±0.2°, 11.45±0.2°, 15.25±0.2°, and 20.51±0.2° in 2θ;

or amorphous form XIX of compound 1 monooxalate, characterized by an X-ray powder diffraction pattern as shown in FIG. 55, and optionally has the following characteristics:

1) In a TGA plot, there is a weight loss of 3.63±0.2% by weight before 105° C.; and a weight loss of 10.4±0.2% by weight between 105° C. and 242° C.;

2) In a mDSC curve, there is a glassy transition temperature at the midpoint temperature of 100.62±2.0° C.;

3) a TGA plot as shown in FIG. 56; and/or 4) a mDSC curve as shown in FIG. 57;

or amorphous form XX of compound 1 dioxalate, characterized by an X-ray powder diffraction pattern as shown in FIG. 58, and optionally has the following characteristics:

1) In a TGA plot, there is a weight loss of 3.52±0.2% by weight before 122° C.; and a weight loss of 11.6±0.2% by weight between 122° C. and 236° C.;

2) In a mDSC curve, there is a glassy transition temperature at the midpoint temperature of 97.8±2.0° C.;

3) a TGA plot as shown in FIG. 59; and/or 4) a mDSC curve as shown in FIG. 60;

or amorphous form XXI of compound 1 dimaleate, characterized by an X-ray powder diffraction pattern as shown in FIG. 61, and optionally has the following characteristics:

1) In a TGA plot, there is a weight loss of 2.29±0.2% by weight before 117° C.; and a weight loss of 8.33±0.2% by weight between 117° C. and 216° C.;

2) In a mDSC curve, there is a glassy transition temperature at the midpoint temperature of 142.29±2.0° C.;

3) a TGA plot as shown in FIG. 62; and/or 4) a mDSC curve as shown in FIG. 63;

or amorphous form XXII of compound 1 ditartrate, characterized by an X-ray powder diffraction pattern as shown in FIG. 64, and optionally has the following characteristics:

1) In a TGA plot, there is a weight loss of 3.14±0.2% by weight before 127.5° C.; and a weight loss of 15.15±0.2% by weight between 127.5° C. and 272.5° C.;

2) In a mDSC curve, there is a glassy transition temperature at the midpoint temperature of 155.97±2.0° C.;

3) a TGA plot as shown in FIG. 65; and/or 4) a mDSC curve as shown in FIG. 66;

or amorphous form XXIII of compound 1 disulfate, characterized by an X-ray powder diffraction pattern as shown in FIG. 67, and optionally has the following characteristics:

1) In the TGA plot, there is a weight loss of 4.77±0.2% by weight before 100° C.;

2) In the mDSC curve, there is a glassy transition temperature at the midpoint temperature of 174.60±2.0° C.;

3) the TGA plot as shown in FIG. 68; and/or 4) the mDSC curve as shown in FIG. 69.

8. The form according to claim 7, wherein the form is amorphous form XIX of compound 1 monooxalate, characterized by an X-ray powder diffraction pattern as shown in FIG. 55, and optionally has the following characteristics:

1) In the TGA plot, there is a weight loss of 3.63±0.2% by weight before 105° C.; and a weight loss of 10.4±0.2% by weight between 105° C. and 242° C.;

3) In the mDSC curve, there is a glassy transition temperature at the midpoint temperature of 100.62±2.0° C.;

3) the TGA plot as shown in FIG. 56; and/or 4) the mDSC curve as shown in FIG. 57.

9. The form according to claim 7, wherein the form is amorphous form XX of the compound 1 dioxalate, characterized by an X-ray powder diffraction pattern as shown in FIG. 58, and optionally has the following characteristics:

1) In the TGA plot, there is a weight loss of 3.52±0.2% by weight before 122° C.; and a weight loss of 11.6±0.2% by weight between 122° C. and 236° C.;

2) In the mDSC curve, there is a glassy transition temperature at the midpoint temperature of 97.8±2.0° C.;

3) the TGA plot as shown in FIG. 59; and/or 4) the mDSC curve as shown in FIG. 60.

10. The form according to claim 7, wherein the form is amorphous form XXI of compound 1 dimaleate, characterized by an X-ray powder diffraction pattern as shown in FIG. 61, and optionally has the following characteristics:

1) In the TGA plot, there is a weight loss of 2.29±0.2% by weight before 117° C.; and a weight loss of 8.33±0.2% by weight between 117° C. and 216° C.;

2) In the mDSC curve, there is a glassy transition temperature at the midpoint temperature of 142.29±2.0° C.;

3) the TGA plot as shown in FIG. 62; and/or 4) the mDSC curve as shown in FIG. 63.

11. The form according to claim 7, wherein the form is amorphous form XXII of compound 1 ditartrate, characterized by an X-ray powder diffraction pattern as shown in FIG. 64, and optionally has the following characteristics:

1) In the TGA plot, there is a weight loss of 3.14±0.2% by weight before 127.5° C.; and a weight loss of 15.15±0.2% by weight between 127.5° C. and 272.5° C.;

2) In the mDSC curve, there is a glassy transition temperature at the midpoint temperature of 155.97±2.0° C.;

3) the TGA plot as shown in FIG. 65; and/or 4) the mDSC curve as shown in FIG. 66.

12. The form according to claim 7, wherein the form is amorphous form XXIII of compound 1 disulfate, characterized by an X-ray powder diffraction pattern as shown in FIG. 67, and optionally has the following characteristics:

1) In the TGA plot, there is a weight loss of 4.77±0.2% by weight before 100° C.;

2) In the mDSC curve, there is a glassy transition temperature at the midpoint temperature of 174.60±2.0° C.;

3) the TGA plot as shown in FIG. 68; and/or 4) the mDSC curve as shown in FIG. 69.

13. A method for preparing the crystalline amorphous form of the salt of compound 1 according to claim 7, comprising:

mixing compound 1 with a solvent and an acid, and suspending and stirring at room temperature at −50° C. to obtain a solid, separating the obtained solid, which is an amorphous form of the salt of compound of 1;

wherein the mass-volume ratio of compound 1 to the solvent is optionally 100 mg: (0.1-10 mL).

14. The preparation method according to claim 13, wherein the acid is selected from hydrochloric acid, sulfuric acid, phosphoric acid, methanesulfonic acid, maleic acid, tartaric acid, benzoic acid, succinic acid and acetic acid.

15. A method for preparing the crystalline form of the salt of compound 1 according to claim 2, comprising:

mixing compound 1 with a solvent and an acid to obtain a solid, separating the obtained solid and drying which is a crystalline form of the salt of the compound 1;

wherein the mass-volume ratio of the compound 1 to the solvent is optionally 100 mg: (0.1-10 mL).

16. The preparation method according to claim 15, wherein the acid is methanesulfonic acid.

17. A pharmaceutical composition comprising the crystalline or amorphous form of the salt of compound 1 according to claim 7 and one or more pharmaceutically acceptable excipients.

Figure 13:
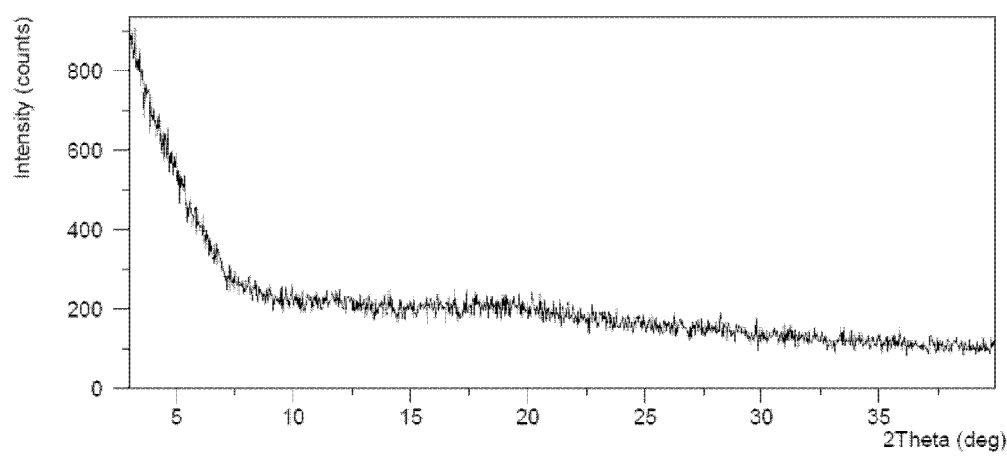
FIG. 13 is an XRPD pattern of Compound 1 dihydrochloride amorphous form V.
Figure 14:
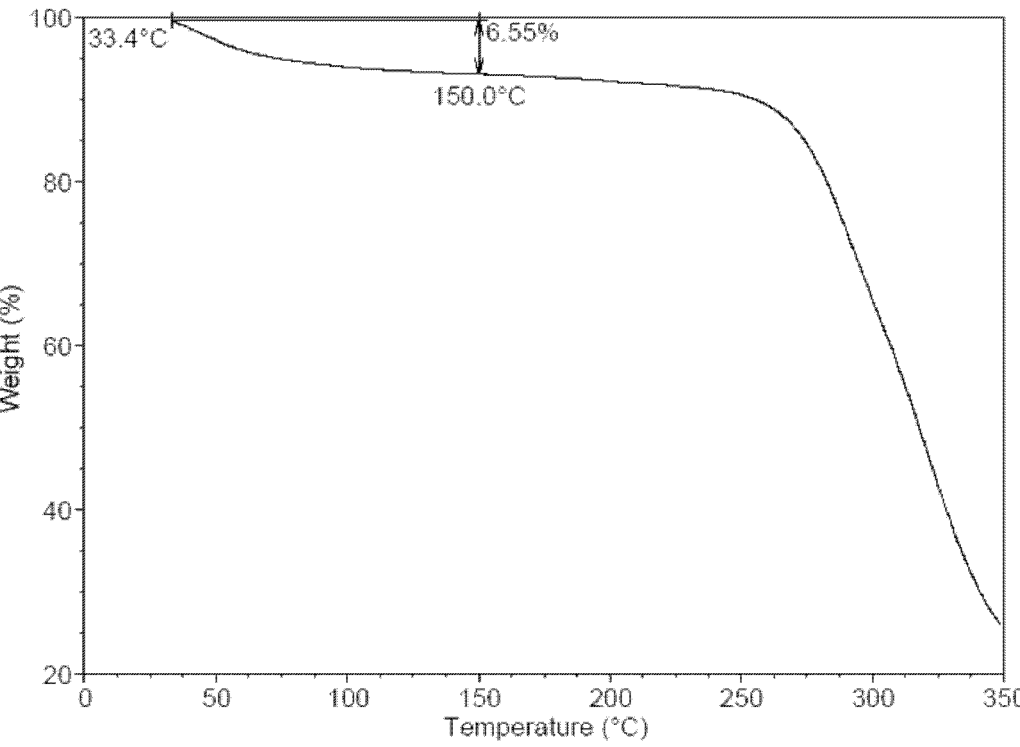
FIG. 14 is a TGA plot of Compound 1 dihydrochloride amorphous form V.
Figure 15:
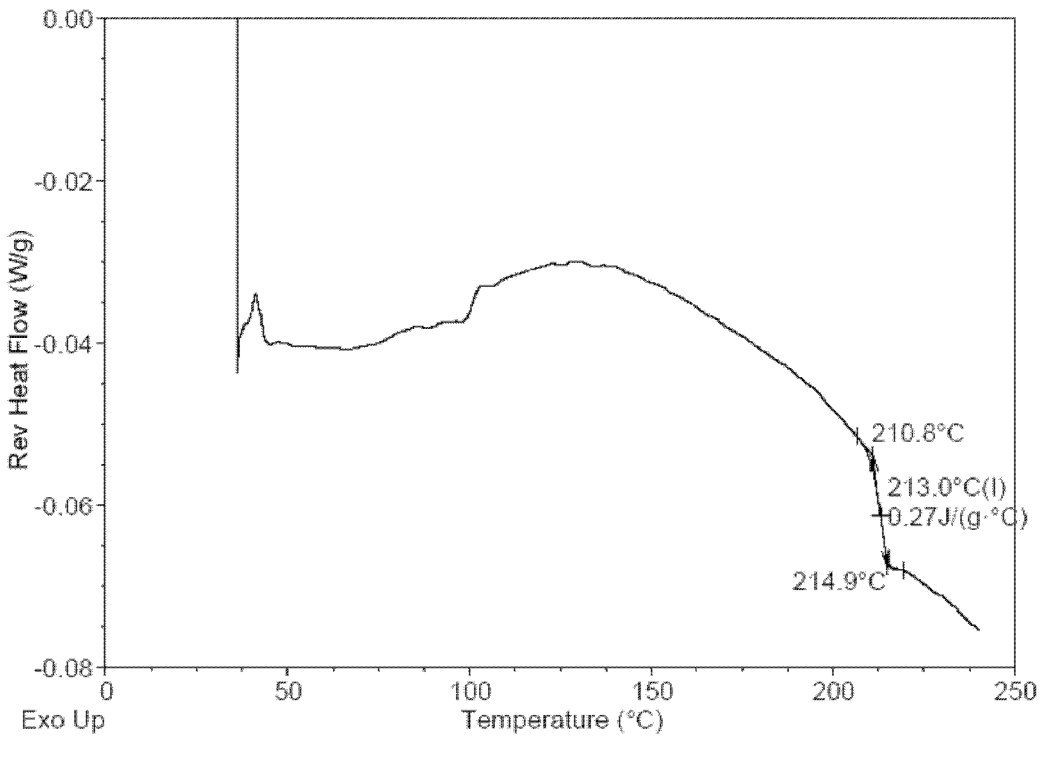
FIG. 15 is a mDSC curve of Compound 1 dihydrochloride amorphous form V.

18. An amorphous form of a salt of compound 1:

(compound 1)

wherein the amorphous form of the salt of compound 1 amorphous form V of compound 1 dihydrochloride, characterized by an X-ray powder diffraction pattern as shown in FIG. 13, and optionally has the following characteristics:

1) In a TGA plot, there is a weight loss of 6.6±0.2% by weight before 150° C.;

2) In a mDSC curve, there is a glassy transition temperature at the midpoint temperature of 213.0±2.0° C.;

3) a TGA plot as shown in FIG. 14; and/or 4) a mDSC curve as shown in FIG. 15.

19. A pharmaceutical composition comprising the amorphous form of the salt of compound 1 according to claim 9 and one or more pharmaceutically acceptable excipients.

20. A method of treating hepatitis A, hepatitis B. hepatitis C, or liver cirrhosis, comprising administering a patient in need thereof a therapeutically effective amount of the amorphous form of the salt of compound 1 according to claim 18.

* * * * *